United States Patent
Zhao et al.

(10) Patent No.: US 12,138,344 B2
(45) Date of Patent: Nov. 12, 2024

(54) THERAPEUTIC pH RESPONSIVE COMPOSITIONS

(71) Applicant: OncoNano Medicine, Inc., Southlake, TX (US)

(72) Inventors: Tian Zhao, Allen, TX (US); Gaurav Bharadwaj, Dallas, TX (US); Xinliang Ding, Grapevine, TX (US); Stephen Gutowski, Irving, TX (US); Jason Miller, Dallas, TX (US); Drew Robinson, Waco, TX (US); Ashley Campbell, Keller, TX (US); Qingtai Su, Allen, TX (US)

(73) Assignee: OncoNano Medicine, Inc., Southlake, TX (US)

( * ) Notice: Subject to any disclaimer, the term of this patent is extended or adjusted under 35 U.S.C. 154(b) by 0 days.

(21) Appl. No.: 17/453,468

(22) Filed: Nov. 3, 2021

(65) Prior Publication Data

US 2023/0026946 A1    Jan. 26, 2023

Related U.S. Application Data

(60) Provisional application No. 63/109,220, filed on Nov. 3, 2020.

(51) Int. Cl.
| | | |
|---|---|---|
| A61K 47/34 | (2017.01) | |
| A61K 9/107 | (2006.01) | |
| A61K 49/00 | (2006.01) | |

(52) U.S. Cl.
   CPC .............. *A61K 9/107* (2013.01); *A61K 47/34* (2013.01); *A61K 49/0056* (2013.01)

(58) Field of Classification Search
   None
   See application file for complete search history.

(56) References Cited

U.S. PATENT DOCUMENTS

| | | |
|---|---|---|
| 2014/0050660 A1 | 2/2014 | Chang et al. |
| 2017/0320993 A1 | 11/2017 | Gao et al. |
| 2018/0110733 A1 | 4/2018 | Irvine et al. |

FOREIGN PATENT DOCUMENTS

| | | |
|---|---|---|
| WO | 2012020096 A1 | 2/2012 |
| WO | 2016168580 A1 | 10/2016 |
| WO | 2019222854 A1 | 11/2019 |

OTHER PUBLICATIONS

Wang et al. (J. Biomed. Opt. 21(7) 078001 (2016)).*
Search Report received in International Application No. PCT/US21/72215 dated Feb. 2, 2022, 3 pages.

* cited by examiner

*Primary Examiner* — Patricia Duffy
*Assistant Examiner* — Garen Gotfredson
(74) *Attorney, Agent, or Firm* — Jeff B. Vockrodt; Culhane PLLC

(57) ABSTRACT

Described herein are therapeutic pH responsive compositions comprising a block copolymer and a therapeutic agent useful for the treatment of cancer.

18 Claims, 30 Drawing Sheets

| Time | PBS 4 °C | | | 10% THL 4 °C | | | 10% THL -80 °C | | |
|---|---|---|---|---|---|---|---|---|---|
| | PDI | Z-Ave (Dh.nm) | Intensity mean (Dh.nm) | PDI | Z-Ave (Dh.nm) | Intensity mean (Dh.nm) | PDI | Z-Ave (Dh.nm) | Intensity mean (Dh.nm) |
| 0 Days | 0.138 | 202 | 175 | - | - | - | - | - | - |
| 1 week | 0.0888 | 183 | 165 | 0.133 | 195 | 173 | 0.114 | 192 | 169 |
| 2 weeks | 0.106 | 185 | 166 | 0.171 | 215 | 182 | 0.132 | 194 | 171 |
| 4 weeks | 0.0759 | 182 | 166 | 0.0696 | 183 | 168 | 0.121 | 187 | 168 |
| 12 weeks | 0.0696 | 160 | 175 | 0.1016 | 167 | 186 | 0.1096 | 169 | 189 |

FIG. 12B

PD = progressive disease, SD = stable disease (-50% to 35%, dO TV), PR = partial response (> 50% decrease, dO TV), CR = complete regression PD = progressive disease, SD = stable disease (-50% to 35%, d0 TV), PR = partial response (> 50% decrease, d0 TV), CR = complete regression BiTE loading quantification by SDS-PAGE

*F*: Feed
*MP*: Encapsulated
*Free*: Unencapsulated

| Characterization | | | |
|---|---|---|---|
| EE (%) | 74 | Size (nm) | 52.8 |
| DL (%) | 14 | PDI | 0.08 |

| Sample | IL-2 in micelle pool /ug | EE |
|---|---|---|
| IL-2(488) | 54 | 77% |
| IL-2(514) | 56 | 77% |
| IL-2(TMR) | 63 | 58% |
| IL-2(647) | 97 | 46% |

Coomassie Stains of Formulations and Column Pools

For each run
Sample 1= Crud mixture
Sample 2= Input
Sample 3 = IL-2 micelle pool
Sample 4 = Free IL-2 pool Very limited Free IL-2 was observed on gel for the modified IL-2

THERAPEUTIC pH RESPONSIVE COMPOSITIONS

PRIORITY

This application claims to U.S. Provisional Patent Application No. 63/109,200 filed on Nov. 3, 2020, and entitled "THERAPEUTIC PH RESPONSIVE COMPOSITIONS," which application is incorporated herein by reference.

BACKGROUND OF THE DISCLOSURE

Multifunctional nanoparticles have received attention in a wide range of applications such as biosensors, diagnostic nanoprobes and targeted drug delivery systems. These efforts have been driven to a large extent by the need to improve biological specificity with reduced side effects in diagnosis and therapy through the precise, spatiotemporal control of agent delivery in various physiological systems. In order to achieve this goal, efforts have been dedicated to develop stimuli-responsive nanoplatforms. Environmental stimuli that have been exploited for pinpointing the delivery efficiency include pH, temperature, enzymatic expression, redox reaction and light induction. Among these activating signals, pH trigger is one of the most extensively studied stimuli based on two types of pH differences: (a) pathological (e.g. tumor) vs. normal tissues and (b) acidic intracellular compartments.

For example, due to the unusual acidity of the tumor extracellular microenvironment (pH ~6.5), several pH-responsive nano systems have been reported to increase the sensitivity of tumor imaging or the efficacy of therapy. However, for polymer micelle compositions that release drug by hydrolysis in acidic environments, it can take days for the release of the drug. In that time period, the body can excrete or break down the micelles.

To target the acidic endo-/lysosomal compartments, nanovectors with pH-cleavable linkers have been investigated to improve payload bioavailability. Furthermore, several smart nanovectors with pH-induced charge conversion have been designed to increase drug efficacy. The endocytic system is comprised of a series of compartments that have distinctive roles in the sorting, processing and degradation of internalized cargo. Selective targeting of different endocytic compartments by pH-sensitive nanoparticles is particularly challenging due to the short nanoparticle residence times (<mins) and small pH differences in these compartments (e.g. <1 pH unit between early endosomes and lysosomes.

Immunotherapy has become a powerful strategy for cancer treatment. Immunomodulators such as interleukin-2 (IL-2) can induce anti-tumor immune responses, but their clinical applications are limited by unfavorable pharmacokinetic properties that can elicit serious dose-limiting toxicities (e.g. vascular leak syndrome).

What is needed are improved pH-responsive micelle compositions for therapeutic applications, in particular compositions having increased drug payloads, prolonged blood circulation times, rapid delivery of drug at the target site, and responsiveness within specific narrow pH ranges (e.g. for targeting of tumors or specific organelles).

SUMMARY OF THE DISCLOSURE

Block copolymers described herein are therapeutic agents useful for the treatment of primary and metastatic tumor tissue (including lymph nodes). The block copolymers and micelle compositions presented herein exploit this ubiquitous pH difference between cancerous tissue and normal tissue and provides a highly sensitive and specific response after being taken up by the cells, thus, allowing the deployment of a therapeutic payload to tumor tissues.

In an aspect described herein is a micelle comprising:
(i) a block copolymer of Formula (III), or a pharmaceutically acceptable salt, solvate, or hydrate thereof:

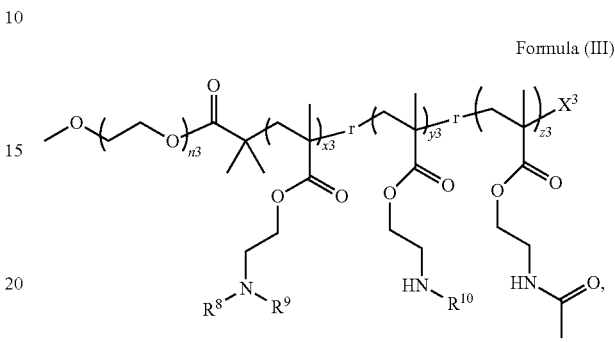

Formula (III)

wherein:
$n_3$ is an integer from 10-200;
$x_3$ is an integer from 40-300;
$y_3$ is an integer from 0-6;
$z_3$ is an integer from 0-10;
$X^3$ is a halogen, —OH, or —C(O)OH;
$R^8$ and $R^9$ are each independently an optionally substituted $C_1$-$C_6$ alkyl, $C_3$-$C_{10}$ cycloalkyl or aryl;
or $R^8$ and $R^9$ are taken together with the corresponding nitrogen to which they are attached to form an optionally substituted 5 to 7-membered ring; and
each $R^{10}$ is independently hydrogen or ICG; and
(ii) a therapeutic agent encapsulated by the block copolymer, wherein the therapeutic agent is a protein conjugated to a fluorescent dye.

In another aspect presented therein, is a micelle composition comprising:
(i) a block copolymer of Formula (IV), or a pharmaceutically acceptable salt, solvate, or hydrate thereof:

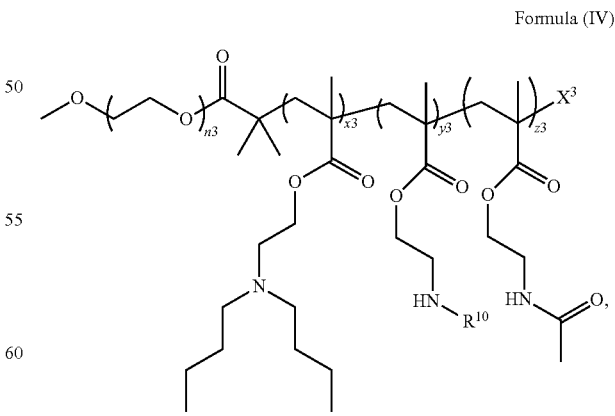

Formula (IV)

wherein:
$n_3$ is an integer from 10-200;
$x_3$ is an integer from 40-300;

$y_3$ is an integer from 0-6;

$z_3$ is an integer from 0-10;

each $R^{10}$ is independently hydrogen or ICG; and $X^3$ is a halogen, —OH, or —C(O)OH; and (ii) a therapeutic agents encapsulated by the block copolymer, wherein the therapeutic agent is a protein conjugated to a fluorescent dye.

In some embodiments, $R^8$ and $R^9$ are each independently —CH$_2$CH$_3$, —CH$_2$CH$_2$CH$_3$, or —CH$_2$CH$_2$CH$_2$CH$_3$. In some embodiments, $R^8$ and $R^9$ are each independently —CH$_2$CH$_2$CH$_2$CH$_3$. In some embodiments, $R^{10}$ is hydrogen. In some embodiments, $R^{10}$ is ICG. In some embodiments, $x_3$ is an integer from 50-200, 60-160, or 90-140. In some embodiments, $x_3$ is 90-140. In some embodiments, $y_3$ is an integer from 1-6, 1-5, 1-4, or 1-3. In some embodiments, $y_3$ is 0. In some embodiments, $z_3$ is an integer from 1-9, 1-8, 1-7, 1-6, 1-5, 1-4, or 1-3. In some embodiments, $z_3$ is 0. In some embodiments, $n_3$ is an integer from 60-150 or 100-140. In some embodiments, $n_3$ is 100-140. In some embodiments, $X^3$ is a halogen. In some embodiments, $X^3$ is —Br. In some embodiments, the protein is a protein of about 5 to about 20 KDa, optionally a cytokine or fragment thereof, or is an antibody optionally an engineered antibody, or a fragment thereof. In some embodiments, the cytokine is an interleukin (IL), chemokine, interferon, lymphokine, monokine, colony stimulating factor, or tumor necrosis factor, optionally an IL-2, IL-1, IL-3, IL-4, IL-5, IL-6, IL-7, IL-8, IL-9, IL-10, IL-11, IL-12, IL-13, IL-15, IL-17, or IL-18 protein, or a fragment thereof. In some embodiments, the antibody or fragment thereof is a bispecific antibody or a fragment thereof or a fusion protein, optionally a bi-specific T-cell engager (BiTE). In some embodiments, the fluorescent dye has an excitation spectrum from about 400 nm to about 900 nm, or about: 400, 450, 500, 550, 600, 650, 700, 750, 800, or 850 nm, optionally coumarin, rhodamine, cyanine, xanthene, fluorescein, or a sulfonated or negatively charged form thereof, or a compound from FIG. 22.

In another aspect, is a method for treating cancer in an individual in need thereof, comprising administration of an effective amount of a micelle composition comprising a therapeutic agent as described herein. In some embodiments, the cancer is a solid tumor. In some embodiments, the cancer comprises a solid tumor. In some embodiments, the tumor is of a cancer, wherein the cancer is of the breast, ovarian, prostate, peritoneal metastasis, colorectal, bladder, kidney, esophageal, head and neck (HNSSC), lung, brain, or skin (including melanoma and sarcoma).

In another aspect, is a method for increasing encapsulation of a therapeutic agent into a micelle, comprising conjugating the therapeutic agent with a fluorescent dye. In some embodiments, the method further comprises contacting the conjugated therapeutic agent with a block copolymer to form the micelle. In some embodiments, the therapeutic agent is a protein of about 5 to about 20 KDa. In some embodiments, the protein is a cytokine or fragment thereof. In some embodiments, the cytokine is an interleukin (IL), chemokine, interferon, lymphokine, monokine, colony stimulating factor, or tumor necrosis factor. In some embodiments, the cytokine is an IL-2, IL-1, IL-3, IL-4, IL-5, IL-6, IL-7, IL-8, IL-9, IL-10, IL-11, IL-12, IL-13, IL-15, IL-17, or IL-18 protein or a fragment thereof. In some embodiments the therapeutic agent is an antibody or a fragment thereof. In some embodiments, the antibody or fragment thereof is a bispecific antibody or a fragment thereof. In some embodiments, the bispecific antibody or fragment thereof is a fusion protein. In some embodiments, the fusion protein is a bi-specific T-cell engager (BiTE). In some embodiments, the fluorescent dye has an excitation spectrum from about 400 nm to about 900 nm. In some embodiments, the fluorescent dye has an excitation spectrum about: 400, 450, 500, 550, 600, 650, 700, 750, 800, or 850 nm. In some embodiments, the fluorescent dye is coumarin, rhodamine, cyanine, xanthene, fluorescein, or a sulfonated or negatively charged form thereof, or a compound from FIG. 22.

Other objects, features and advantages of the block copolymers, micelle compositions, and methods described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

evidenced by large proportion of IL-2 (800CW) in unencapsulated free IL-2 pool. This confirms importance of electrostatic interaction by seeing if performing PDBA IL-2 (800CW) formulation at high ionic strength conditions attenuates encapsulation efficiency. Both unlabeled and 800CW labeled IL-2 were loaded into PEG-PLA nanoparticles at ~20% EE, 2% DL compared to ~80% EE, 8% DL for PDBA.

Figure 1:
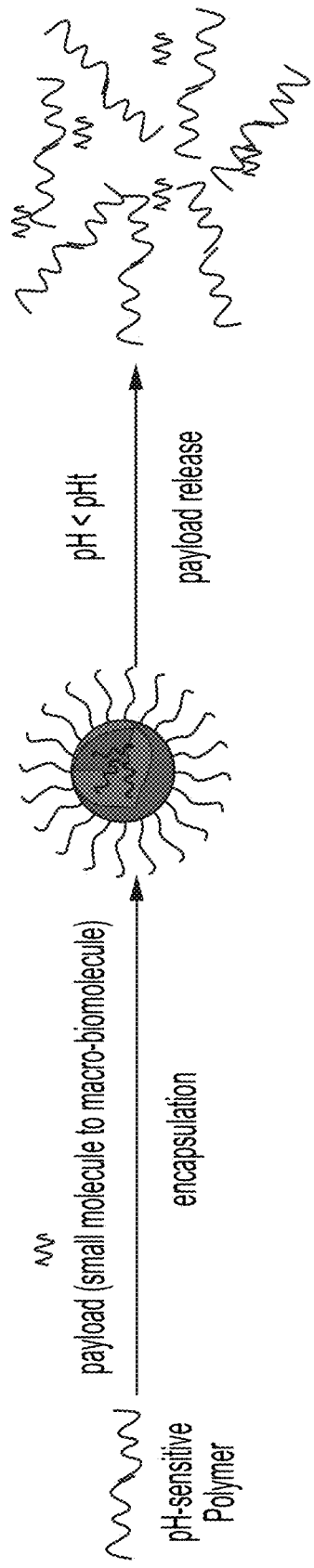
FIG. 1 displays a schematic of an ultra-pH sensitive nanoparticle platform which enables pH-dependent release of payloads (e.g. IL-2). When pH>pH$_t$, block copolymers exists as nanoparticles; once pH<pH$_t$, the nanoparticles disassemble into unimers, thereby releasing the encapsulated payloads.
Figure 2:
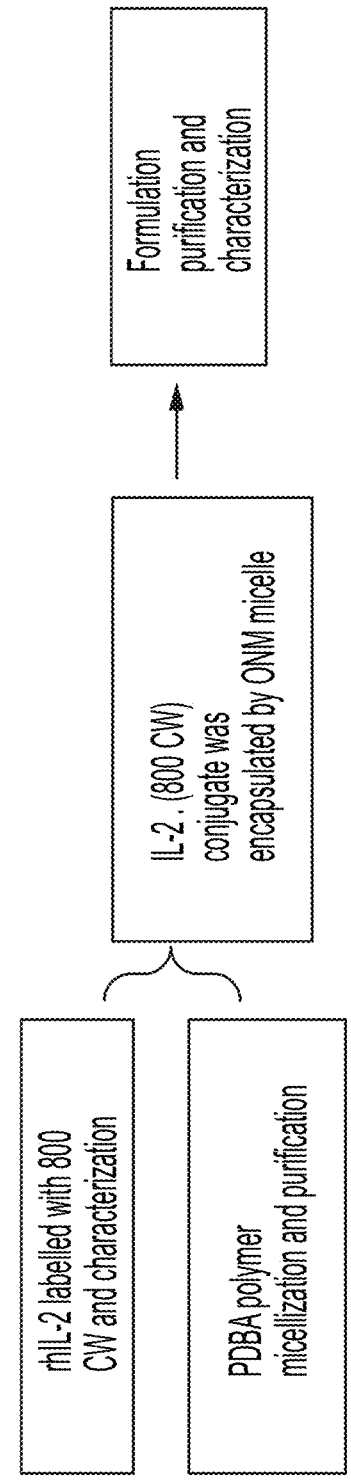
FIG. 2 displays a scheme for a non-covalent formulation with micelles and 800CW IL-2 by simple mixing.
Figure 3:
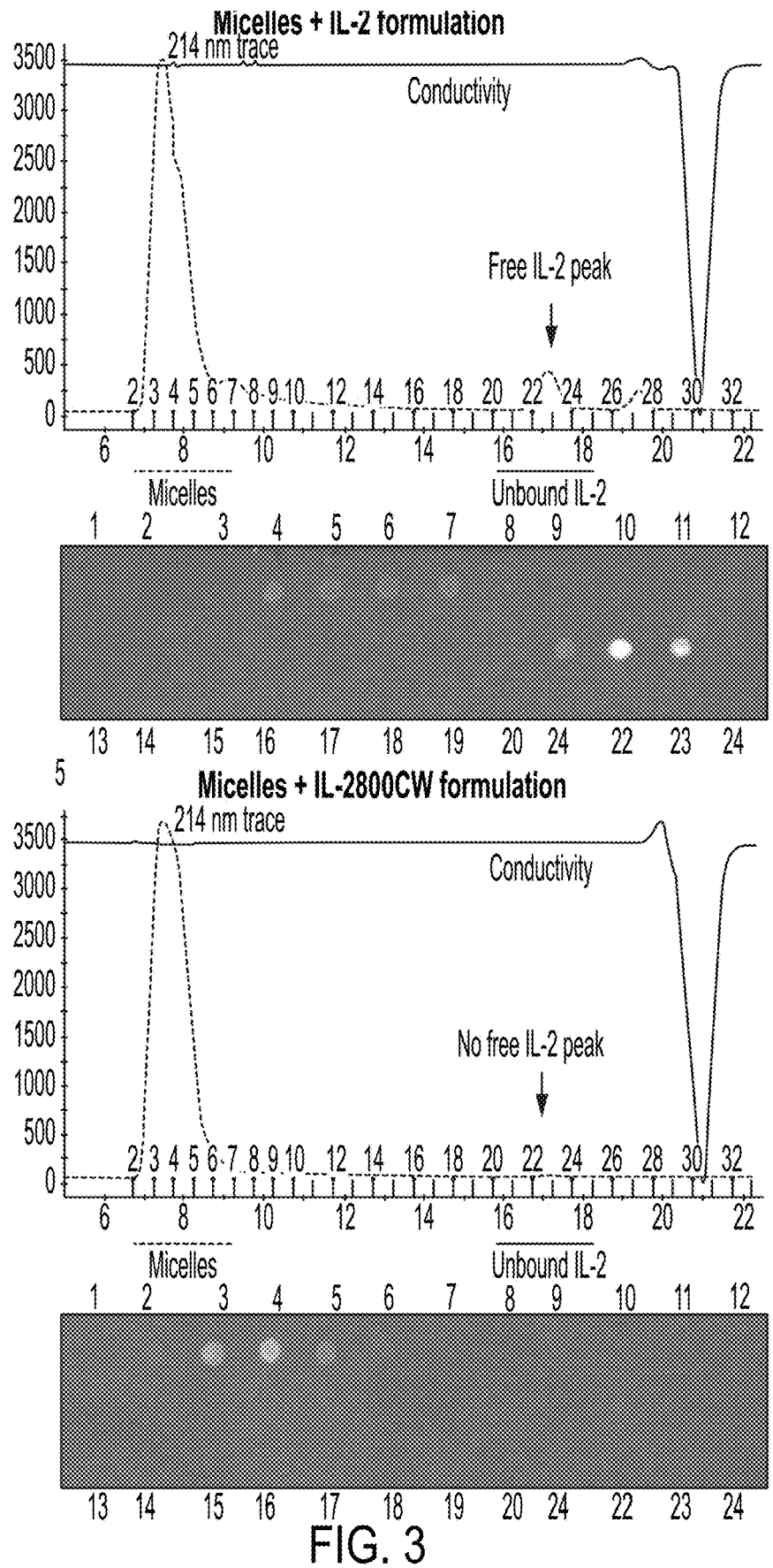
FIG. 3 shows that PEG$_n$-PDBA$_{160}$ micelles can be used to prepare formulations of both IL-2 (unmodified) and IL-2 (800CW). Modified IL-2 (800CW) formulations have better encapsulation efficiency than IL-2 formulations. (97% of IL-2 (800CW) recovered was found associated with micelle fractions vs 11% for IL-2) as evaluated by dot blot against IL-2.
Figure 4:
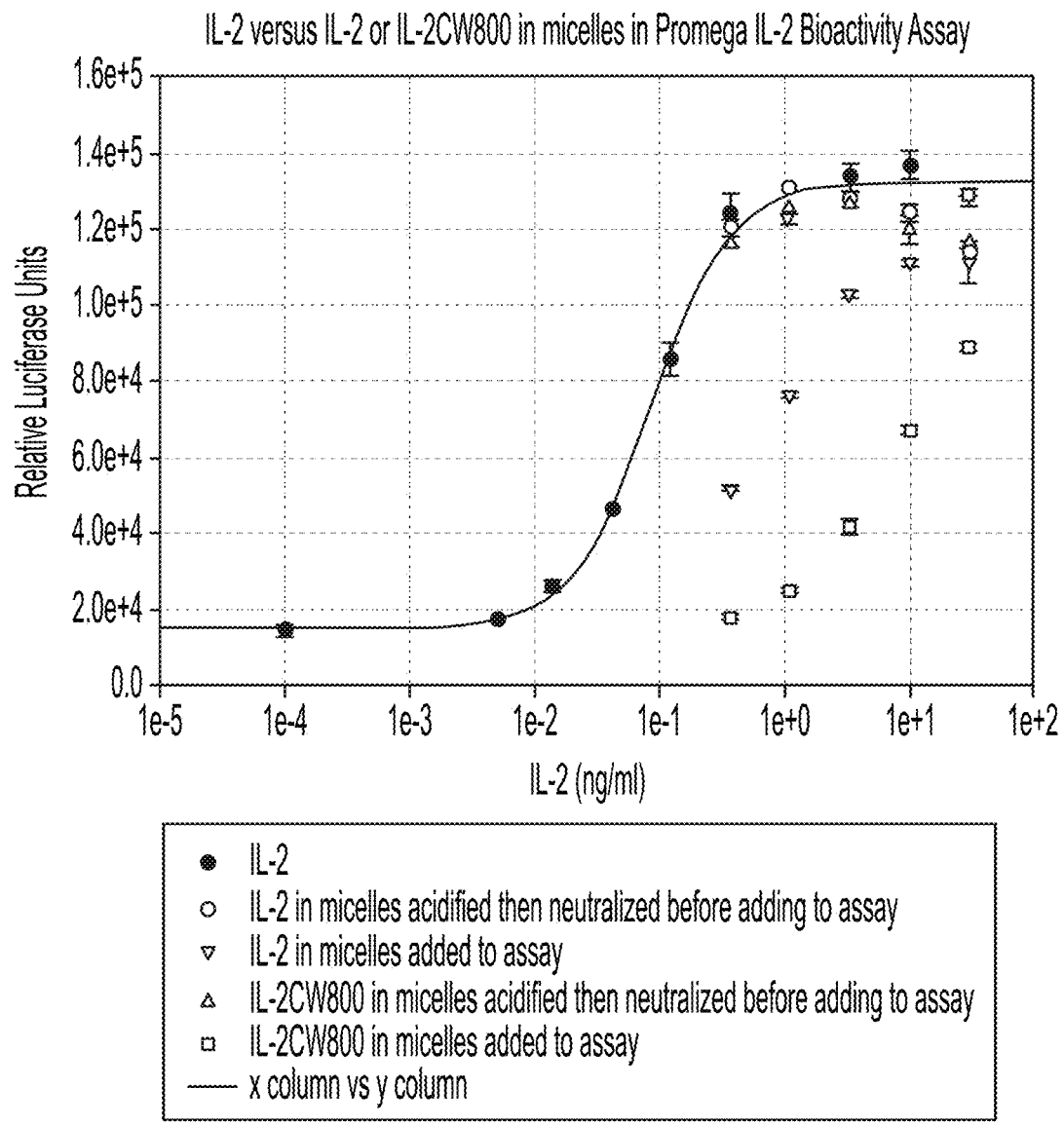
FIG. 4 shows encapsulated formulations with bioactivity of both rhIL-2 (unmodified) and modified IL-2 (800CW). Micelles better protection in neutral state of IL-2 (800CW) (black square) compared to IL-2 (black inverted triangle) while both formulations show similar bioactivity on acidification. Micelles encapsulate and release both IL-2 and IL-2 (800CW) in a pH responsive manner.
Figure 5:
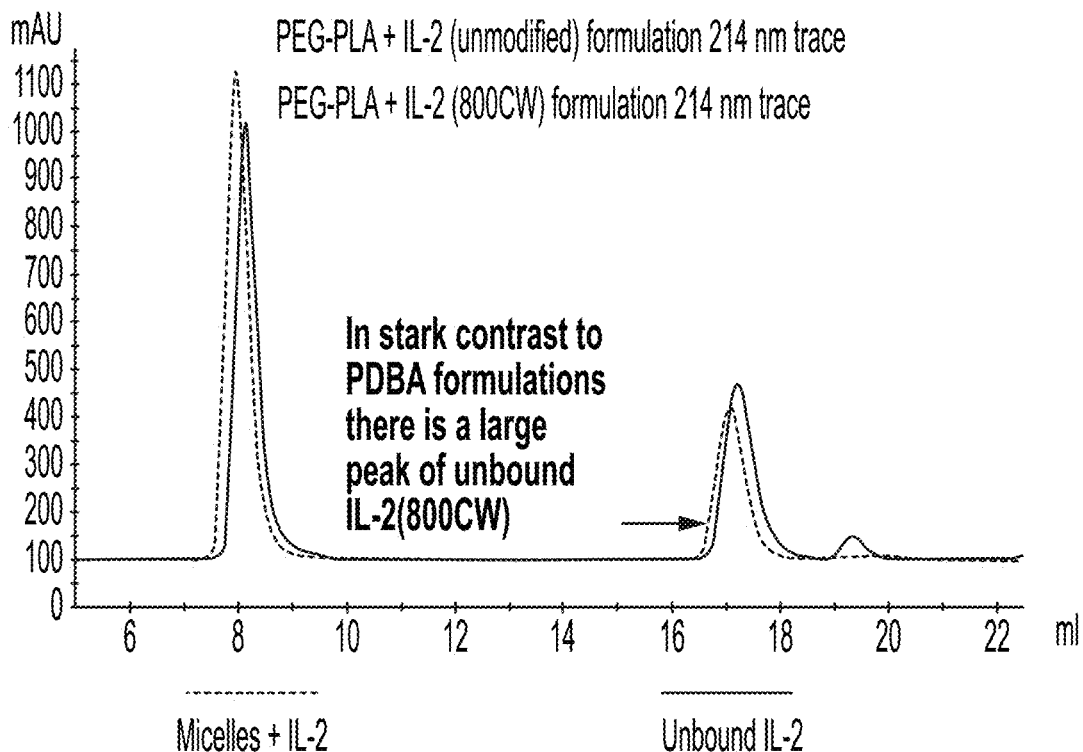
FIG. 5 shows that PEG5K-PLA16K is inefficient at IL-2 (modified or unmodified) encapsulation, compared to PEG-PDBA. 800CW modification has to pair with the pH-sensitive micelles described herein to increase loading of IL-2. Even when IL-2 is modified with 800CW, non-pH sensitive micelles like PEG-PLA cannot encapsulated IL-2 efficiently.
Figure 6:
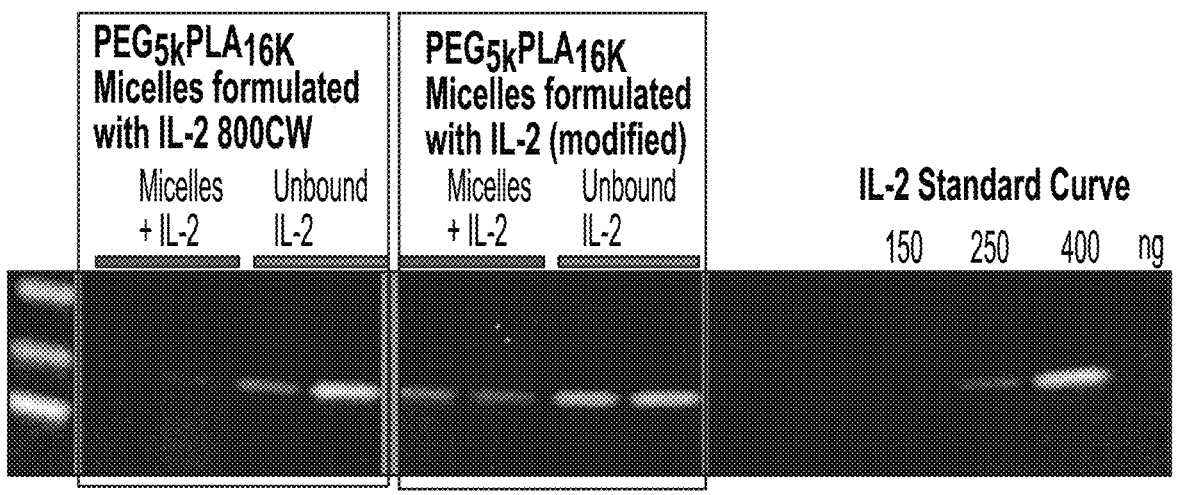
FIG. 6 shows Coomassie stain of micelle encapsulated IL-2 peak and free IL-2 peak from non-pH sensitive micelles formulations made with IL-2 or IL-2 (800CW). PDBA>>PEG5K-PLA15K at encapsulating IL-2 (800CW)
Figure 7:
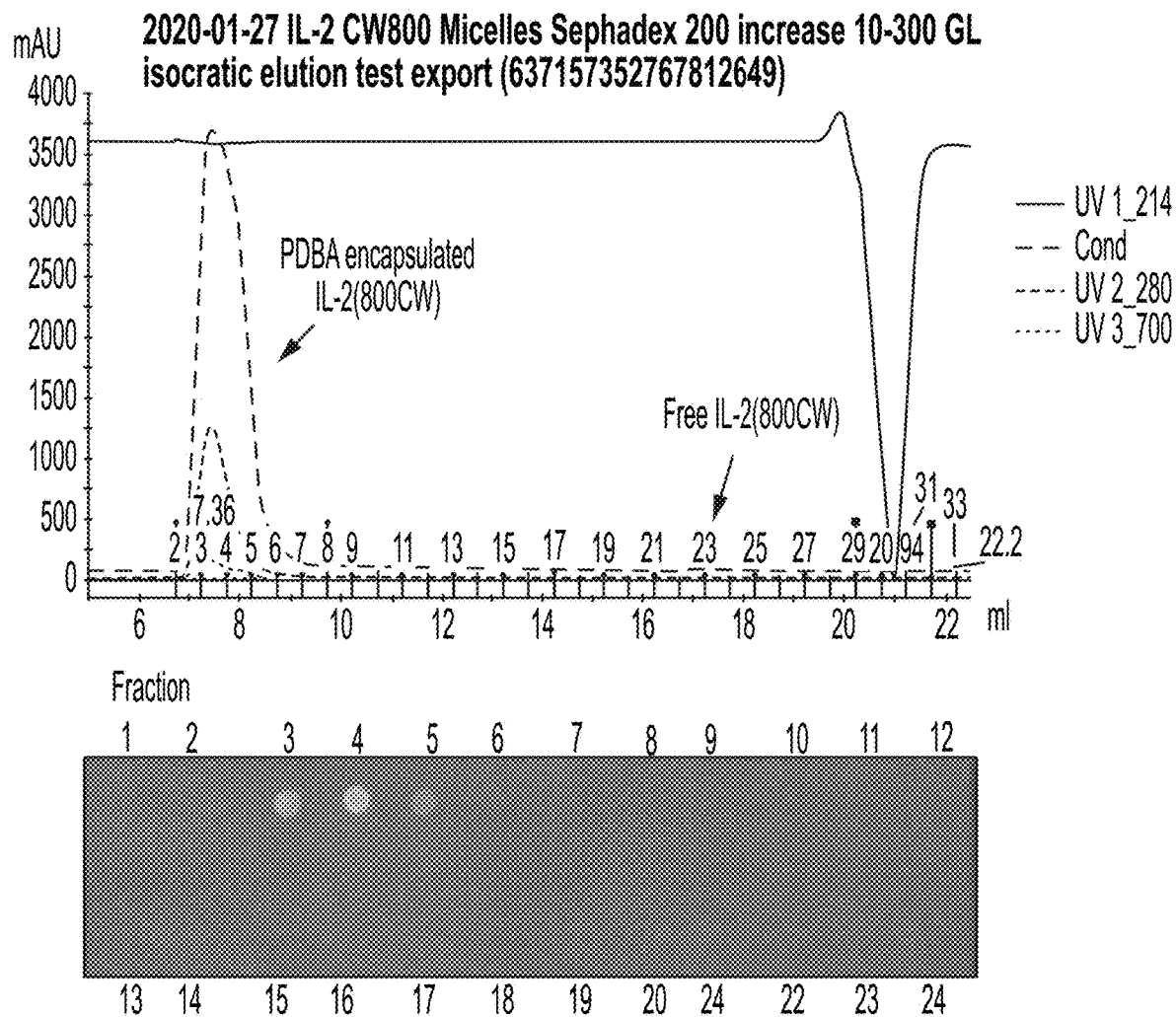

FIG. 7 shows purification of non-covalent PDBA encapsulated IL-2 (800CW) formulations by FPLC on Superdex 200 column. (Top): FPLC chromatogram of non-covalent formulation and (Bottom): Dot blot for IL-2 of FPLC fractions shows minimal free IL-2.

Figure 8A:
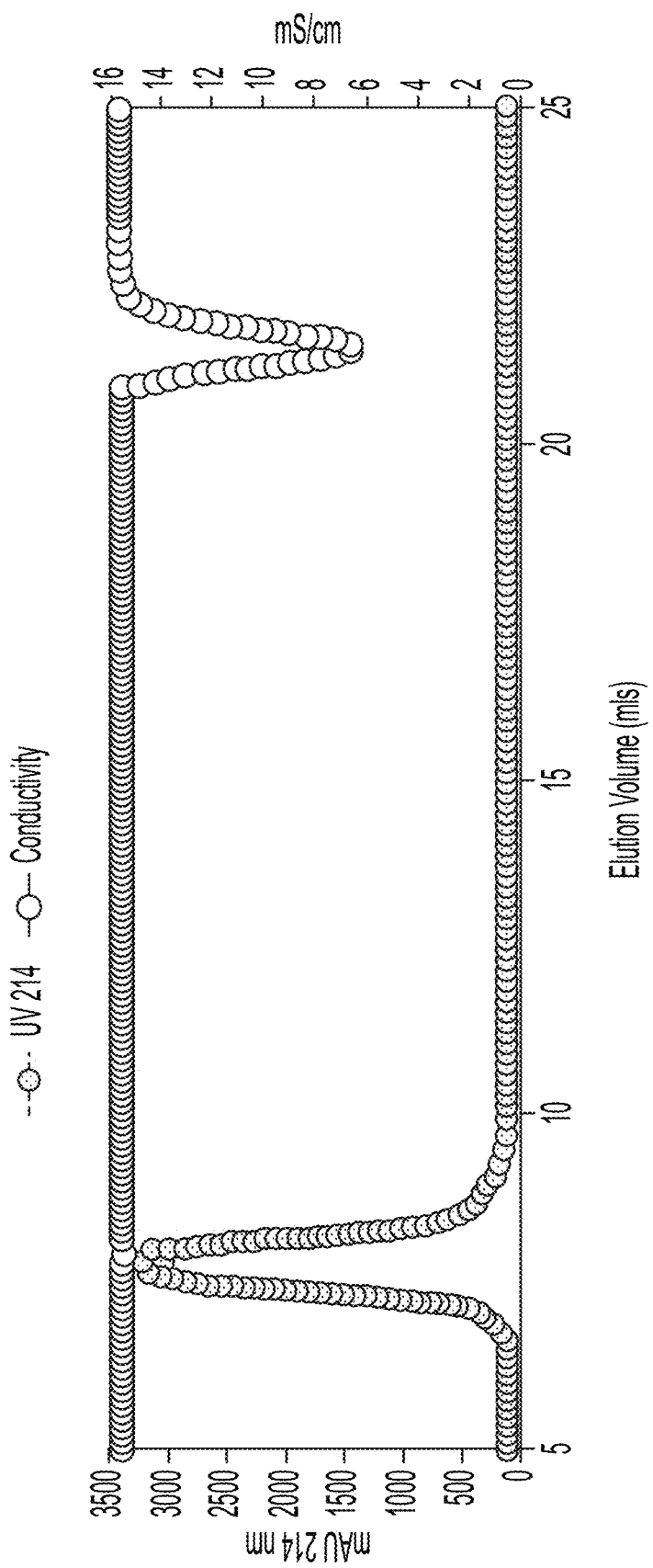
Figure 8B:
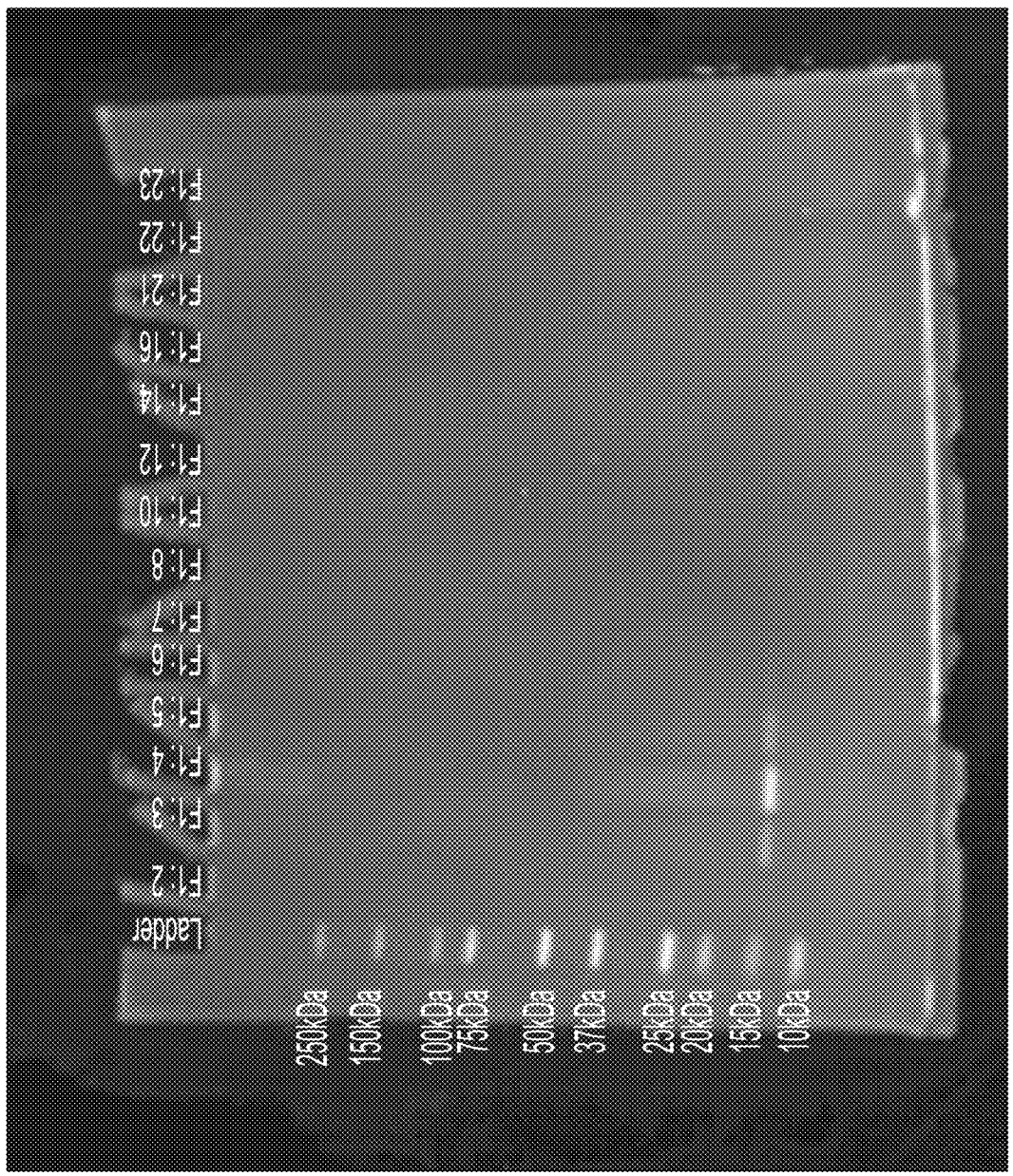

FIG. 8 shows IL-2 (800CW) loading is stable in the complex as no free IL-2 (800CW) leaks out of purified formulations after FPLC reinjection. (Top panel): FPLC chromatogram, Right: SDS-PAGE and (Bottom panel): Coomassie staining of FPLC fractions. IL-2 migrates ~15 kDa.

Figure 9:
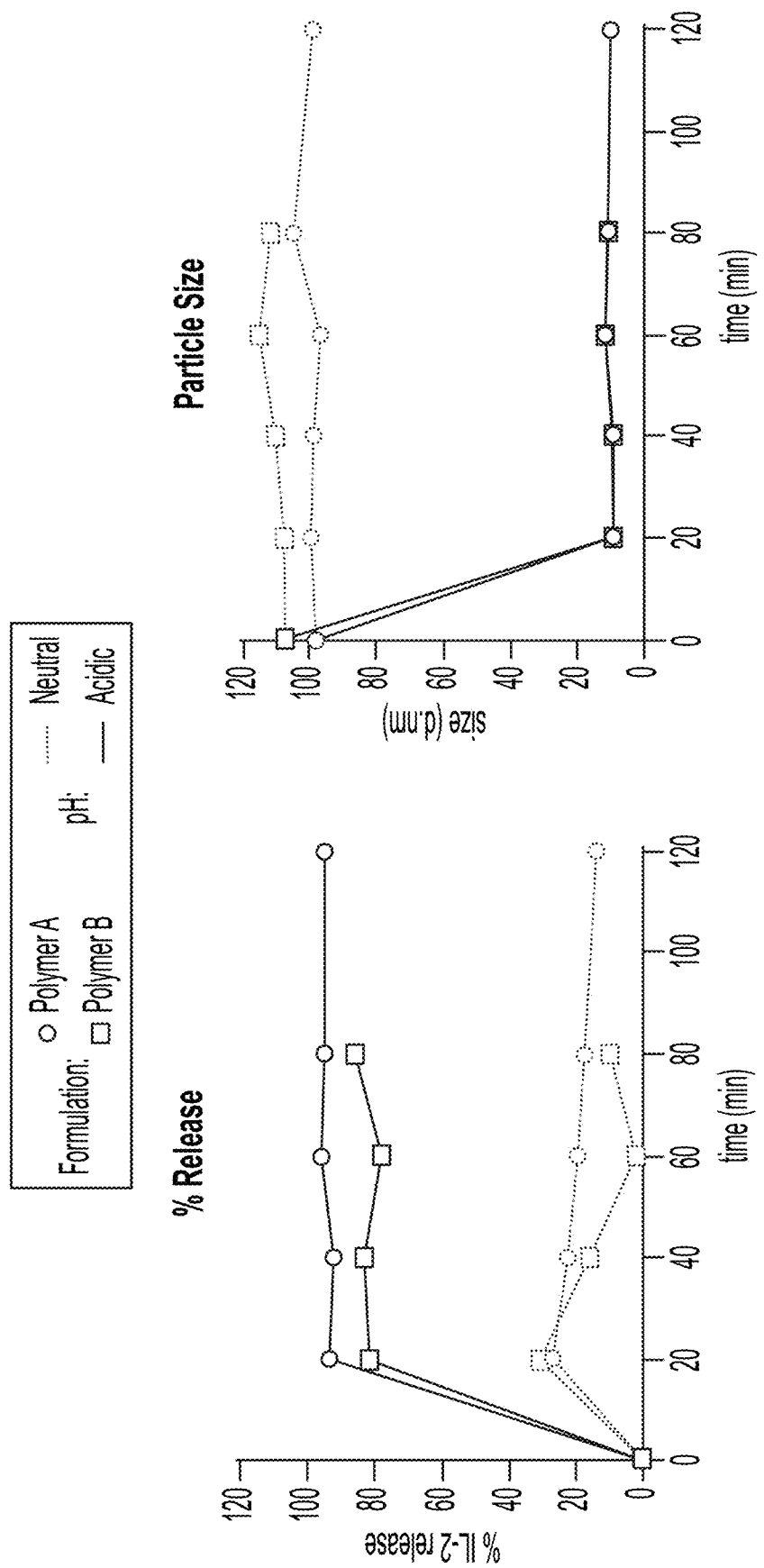

FIG. 9 shows a pH-dependent IL-2 release profile. (Left panel) Quantitative measurement of acidic buffer triggered IL-2 payload release. (Right panel): Size change of nanoparticles under acidic buffer conditions tested by DLS.

Figure 10:
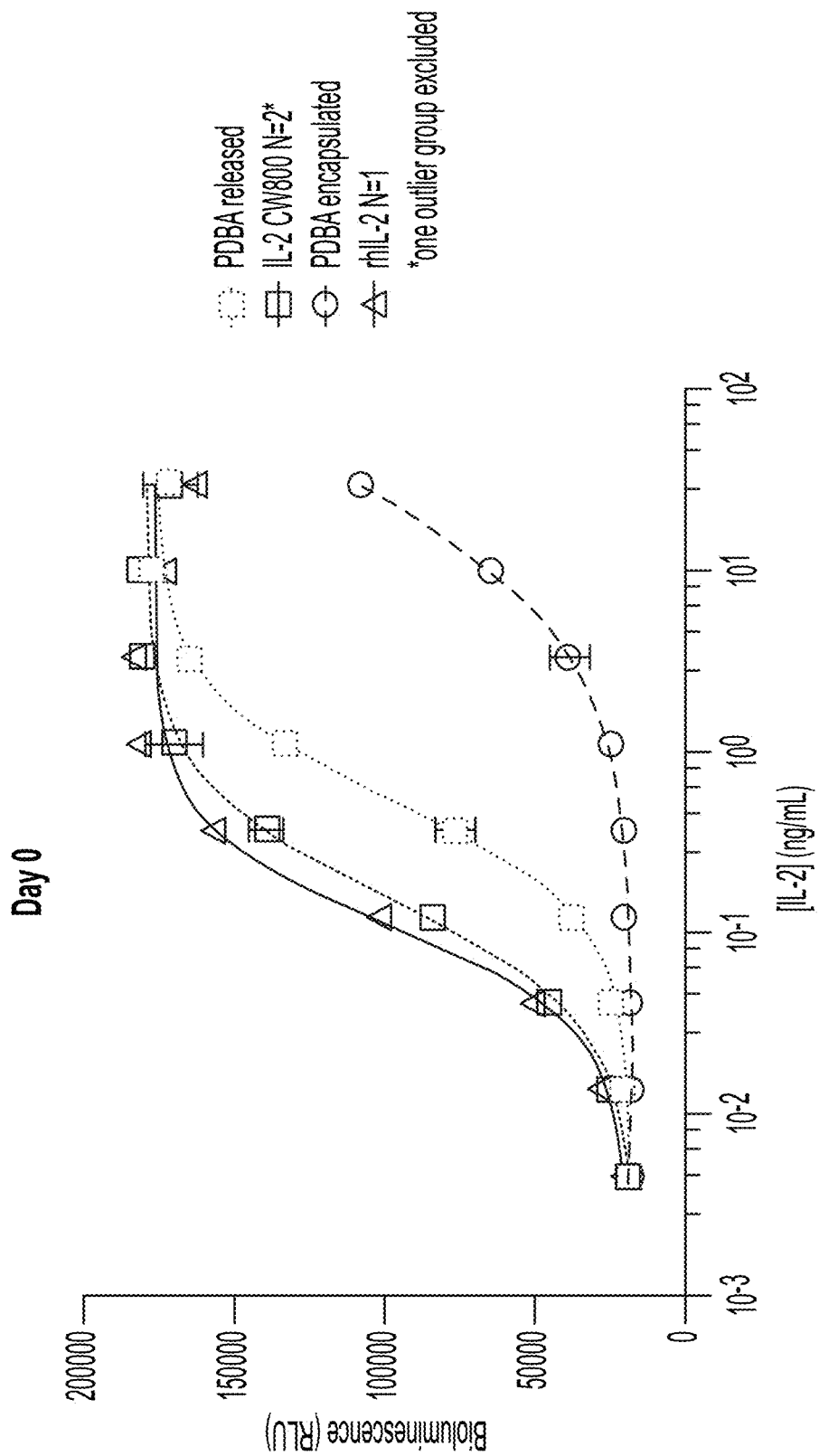

FIG. 10 shows the bioactivity of non-covalent formulations in IL-2(800CW) bioassay. Nanoparticles encapsulating IL-2 (800CW) effectively mitigate bioactivity at neutral pH (open circles). Once acidified, IL-2 (800CW) bioactivity is returned close to wild-type levels (gray triangles).

Figure 11A:
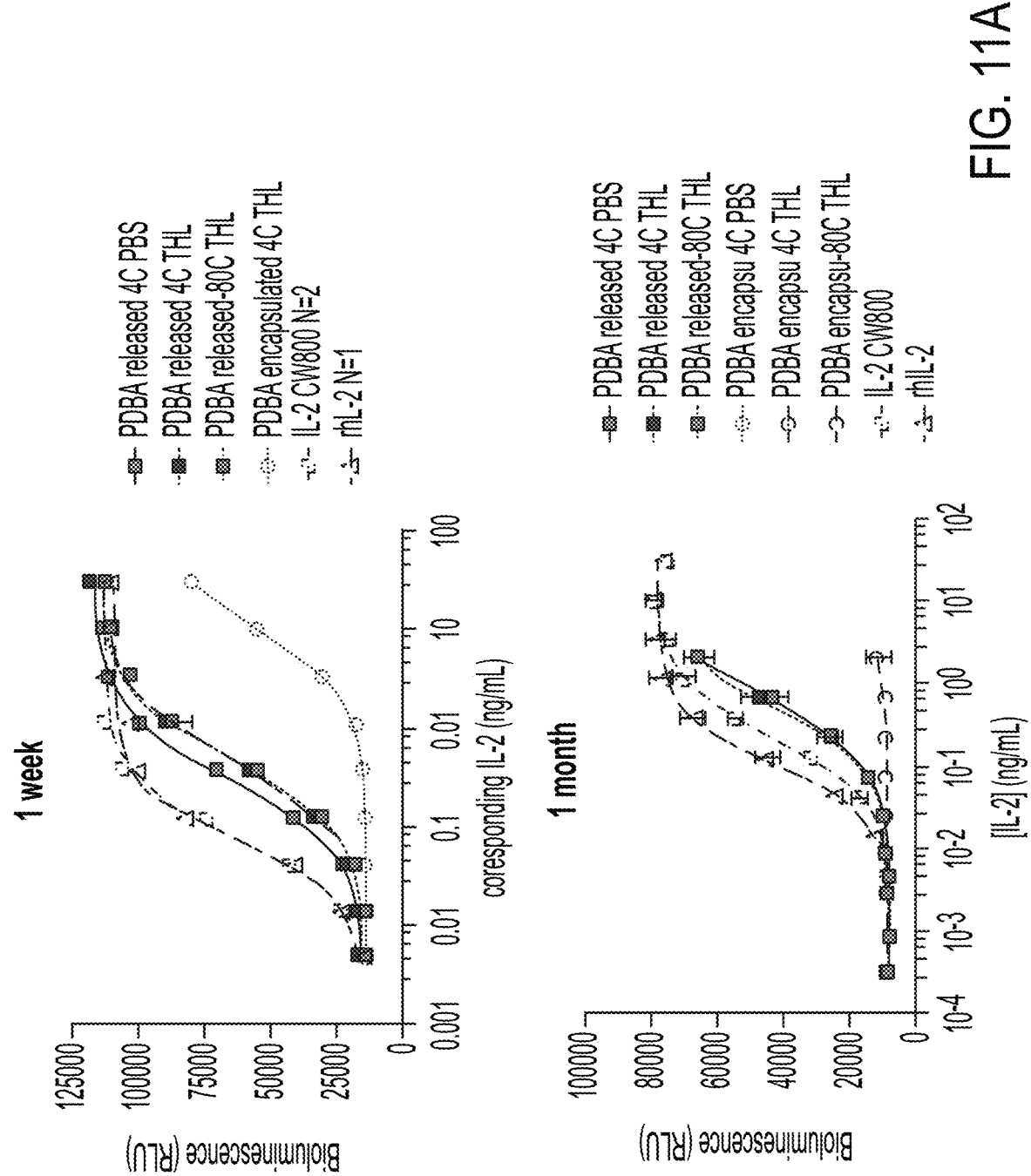
Figure 11B:
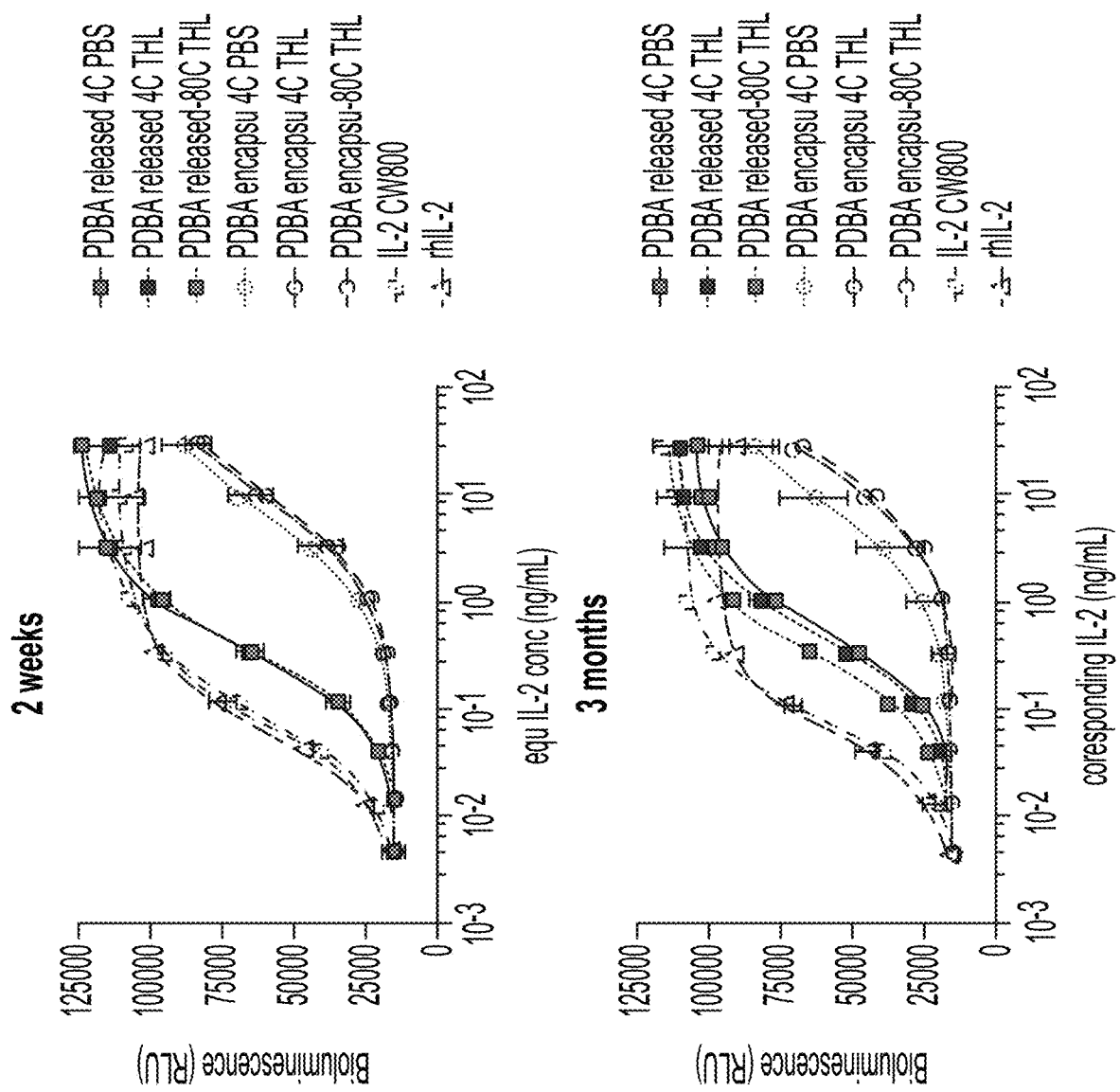

FIG. 11 shows the stability of bioactivity of PDBA-IL-2 (800CW) non-covalent formulations. Bioactivity of a PDBA micelle was evaluated in the bioassay over 3 months for IL-2 (800CW) bioactivity and showed consistent ON/OFF characteristics and consistent bioactivity.

Figure 12A:
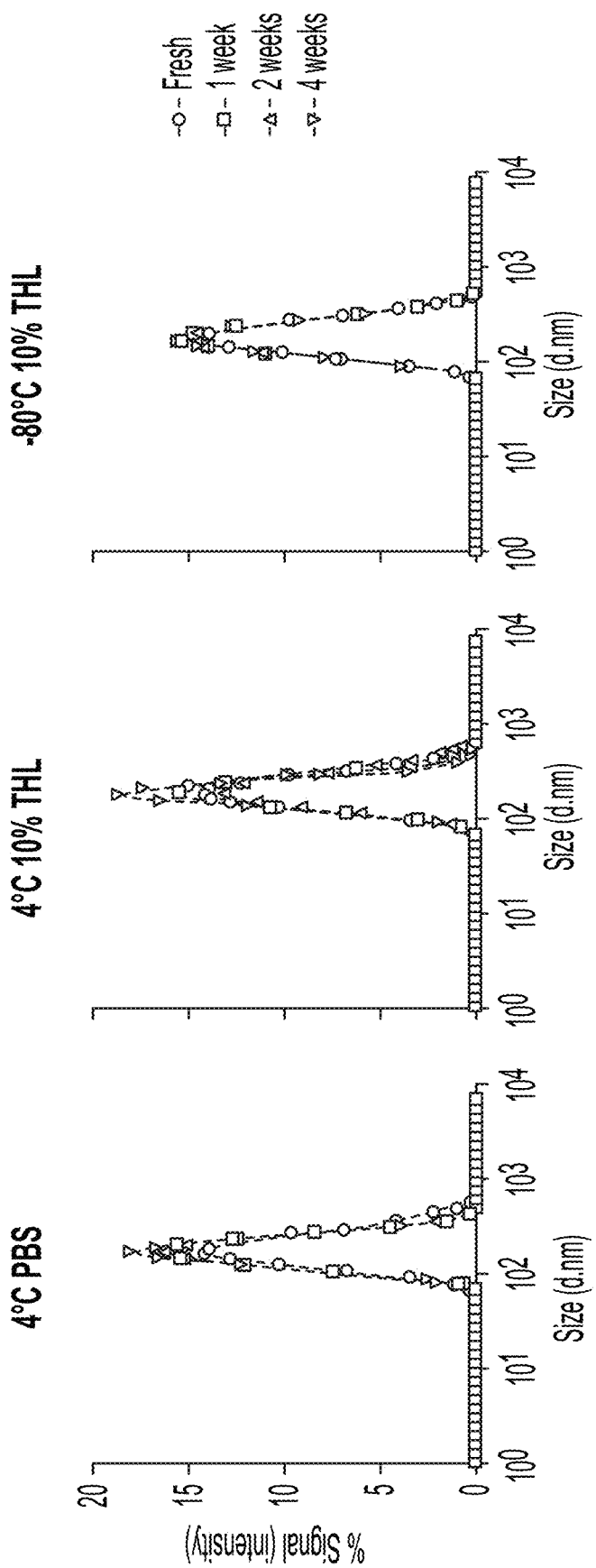

FIG. 12 shows that micelle encapsulated IL-2 (800CW) formulations show good shelf-life in multiple storage conditions. The PDBA encapsulated IL-2 (800CW) formulations are stable by size for at least 3 months of storage in the indicated conditions.

Figure 13:
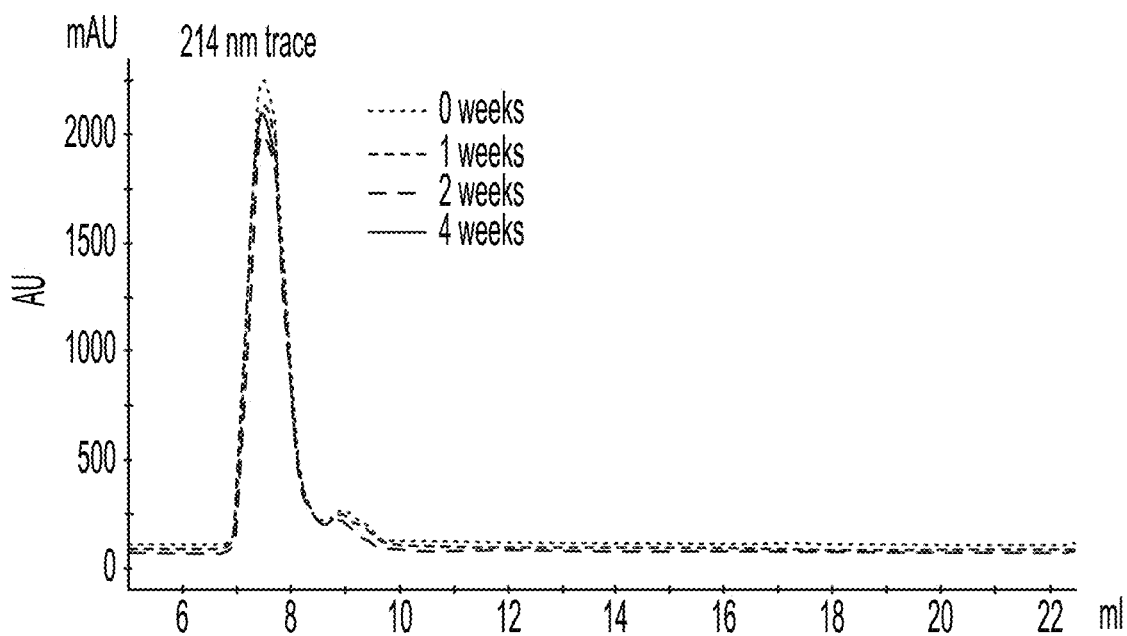
Figure 13:
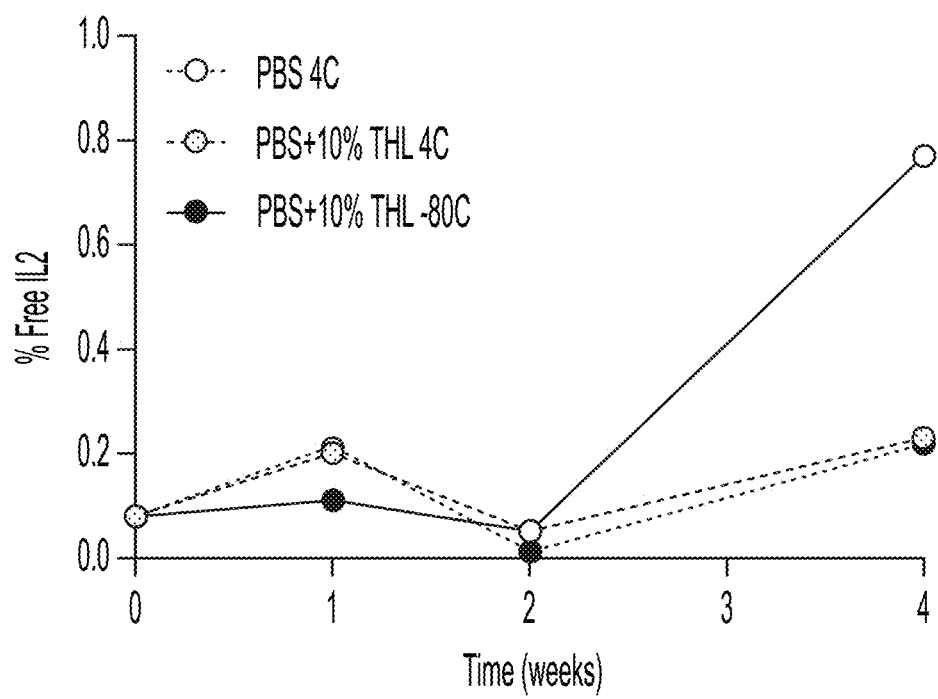

FIG. 13 shows that PDBA encapsulated IL-2(800CW) formulations show good shelf-life in multiple storage conditions. PDBA-IL-2 (800CW) stability was evaluated for IL-2 (800CW) leaking from nanoparticles by FPLC trace and quantitation of dot blot/western blot. (Top panel): A representative series of traces (214 nm) for PBS 4C samples shows no free IL-2 (800CW) expected around 17 mL elution volume while micelle peak does not change shape or elution time with extended storage under any condition. (Bottom panel): Quantitation of immunoblots for IL-2 show <1% of IL-2 (800CW) elutes as free protein in any storage condition.

Figure 14A:
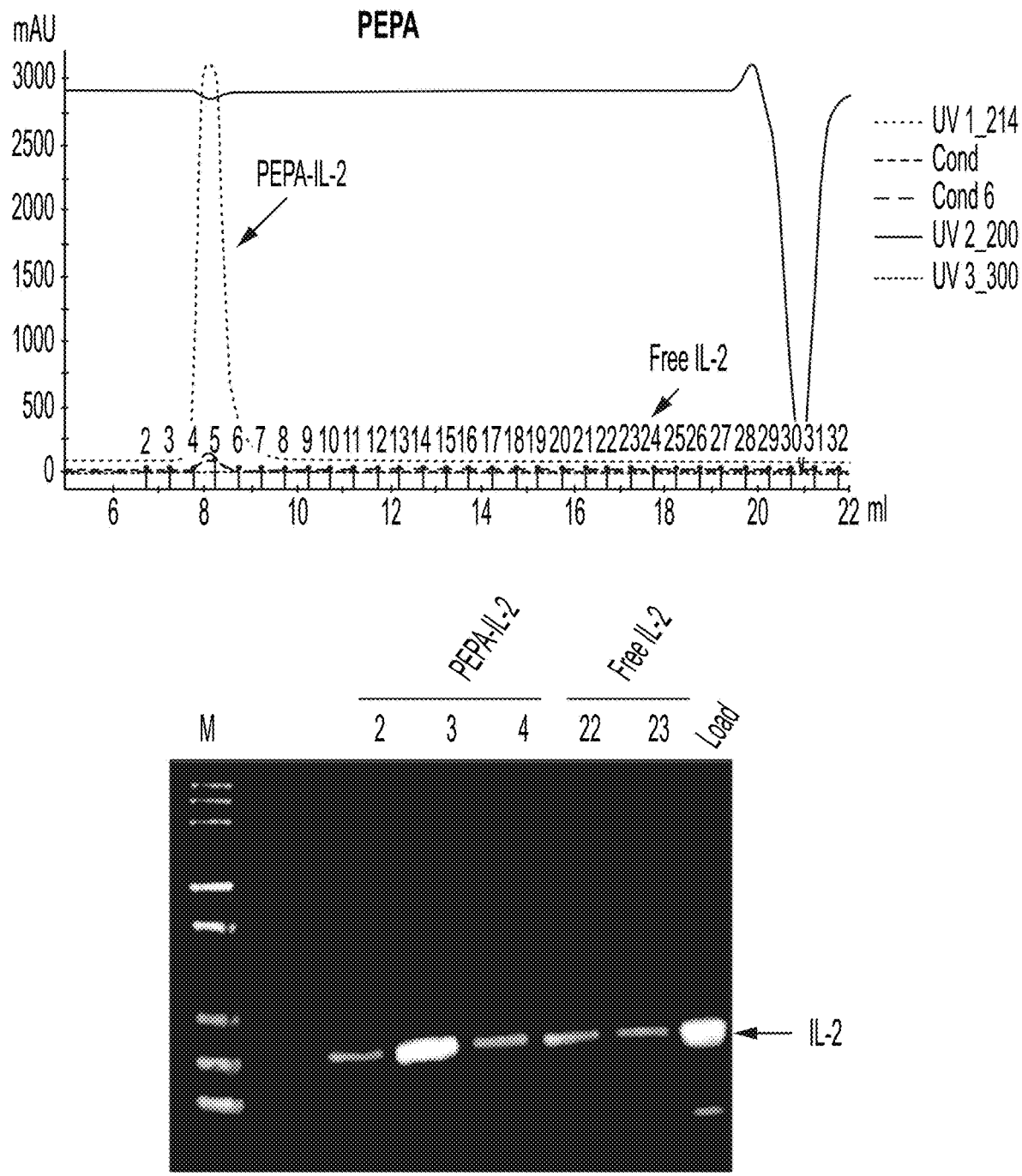
Figure 14B:
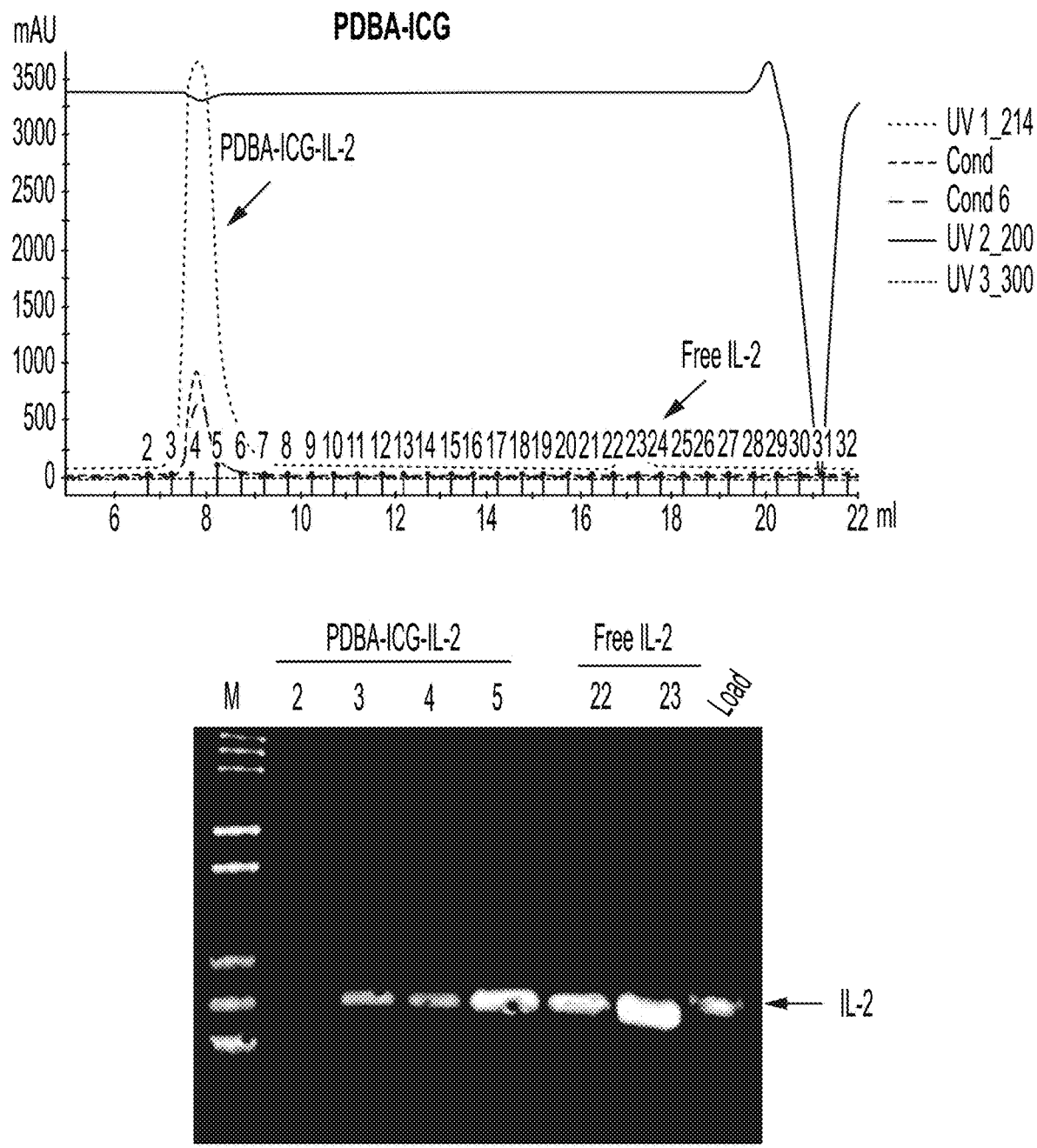

FIGS. 14A and 14B shows the IL-2 (800CW) can be non-covalently encapsulated in block copolymer micelles with different chemical structures. (14A) PEPA and (14B) PDBA-ICG micelles efficiently load IL-2(800CW). Purifications were performed on an Akta Pure equipped with Superdex 200 increase column. IL-2 (800CW) content of each fraction was confirmed by western blot.

Figure 15:
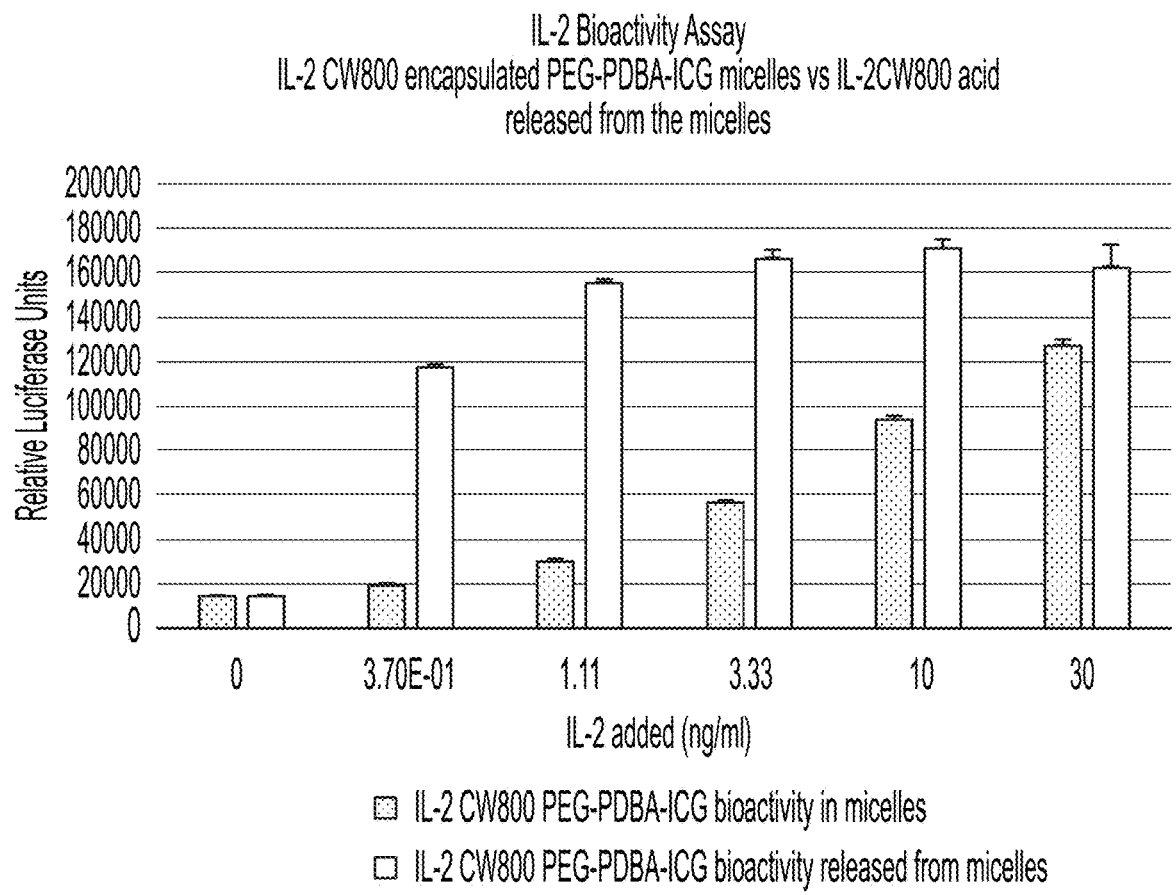
Figure 15:
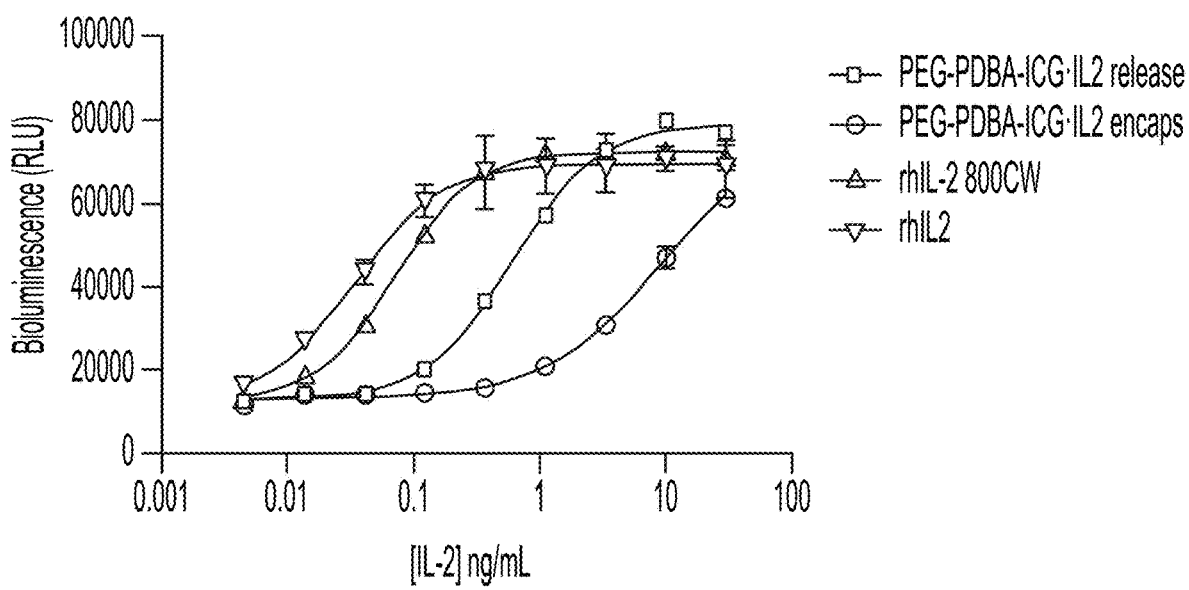

FIG. 15 shows ICG-conjugated PDBA micelles can load and release IL-2 (800CW) effectively. PEG-PDBA-ICG can effectively release biologically active IL-2 (800CW) in a pH responsive manner (Top plot): orange bars versus blue bars, right plot open circles vs closed squares). (Bottom plot): shows characterization of fresh formulations and right panel shows characterization of particles after ~6 months storage at 4C in PBS.

Figure 16:
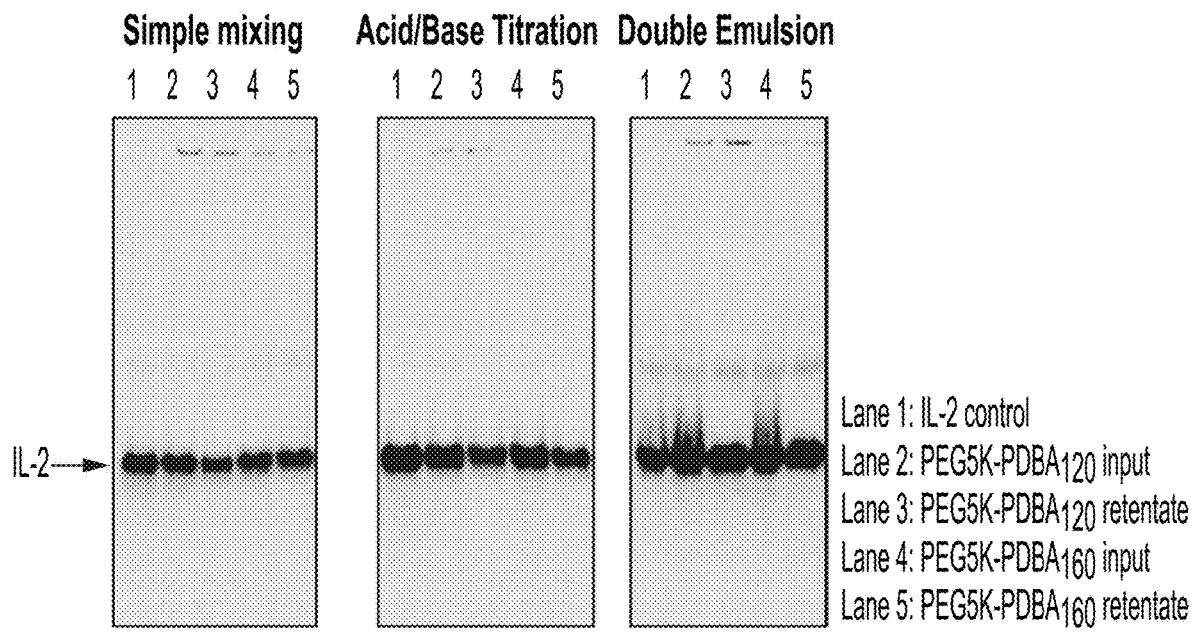
Figure 16:
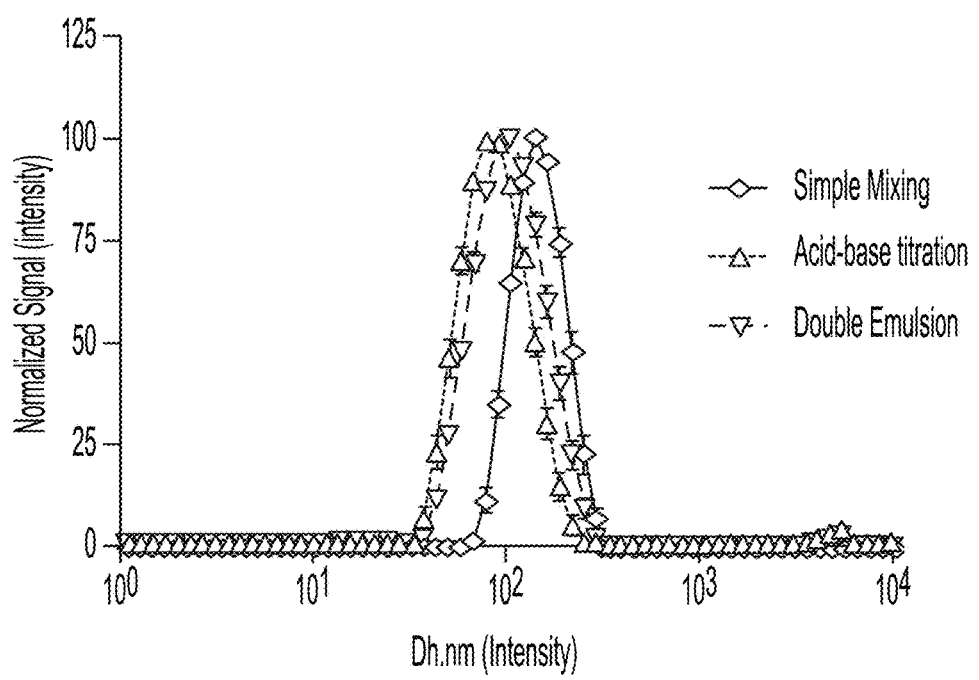

FIG. 16 shows that micelles can be loaded by IL-2 (800CW) by different noncovalent formulation methods. Loading was performed by acid/base titration, simple mixing, and double emulsion solvent evaporation methods. (Left pane): IL-2 (800CW) loading in retentate fraction was confirmed by SDS-PAGE after spin-column purification. Detection was performed by 800CW fluorescence using a LI-COR pearl. (Right panel): DLS characterization of representative samples of PEG5K-PDBA160 formulated with IL-2 800CW with different formulation methods.

Figure 17:
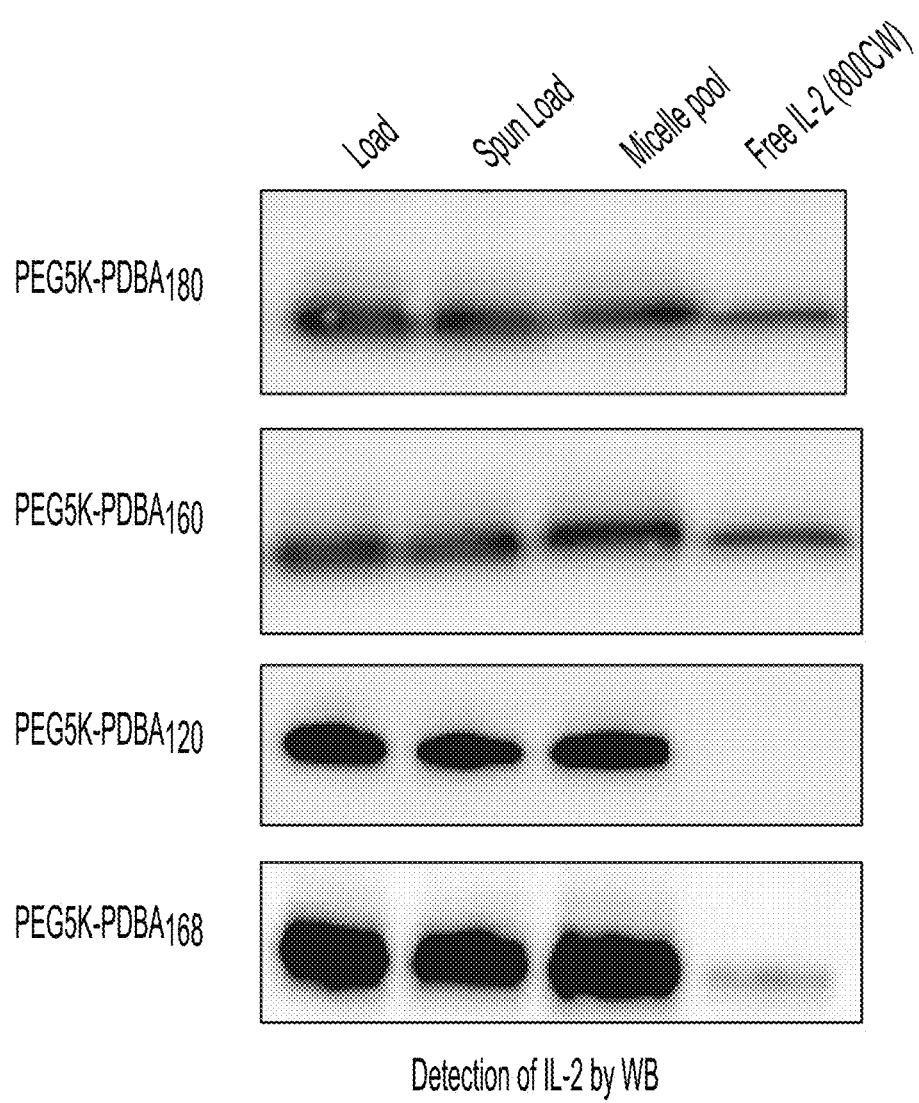
Figure 18A:
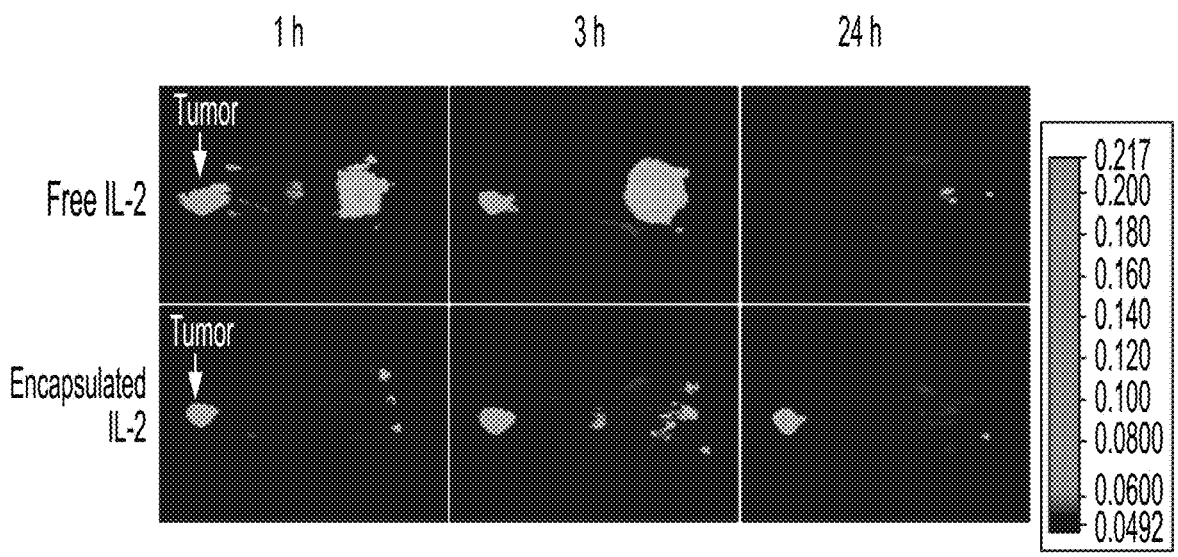
Figure 18B:
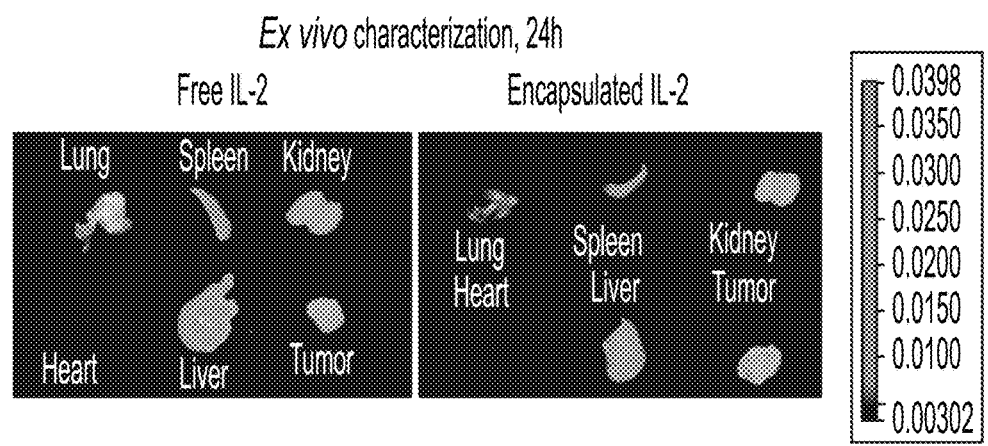
Figure 18C:
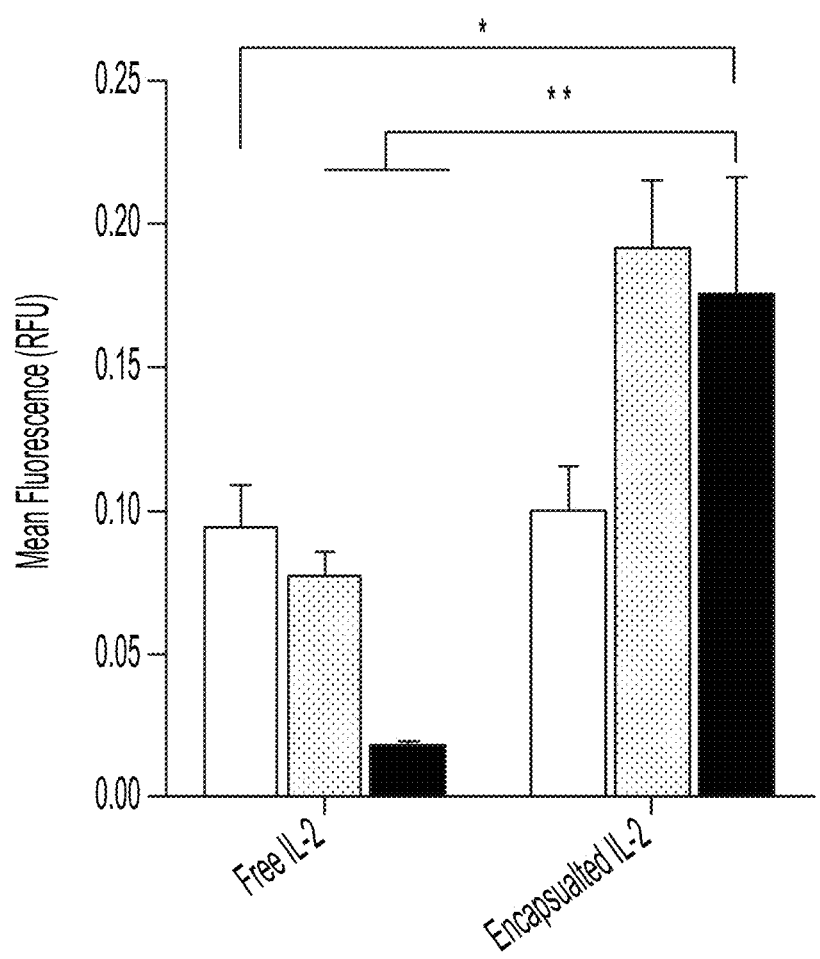
Figure 18D:
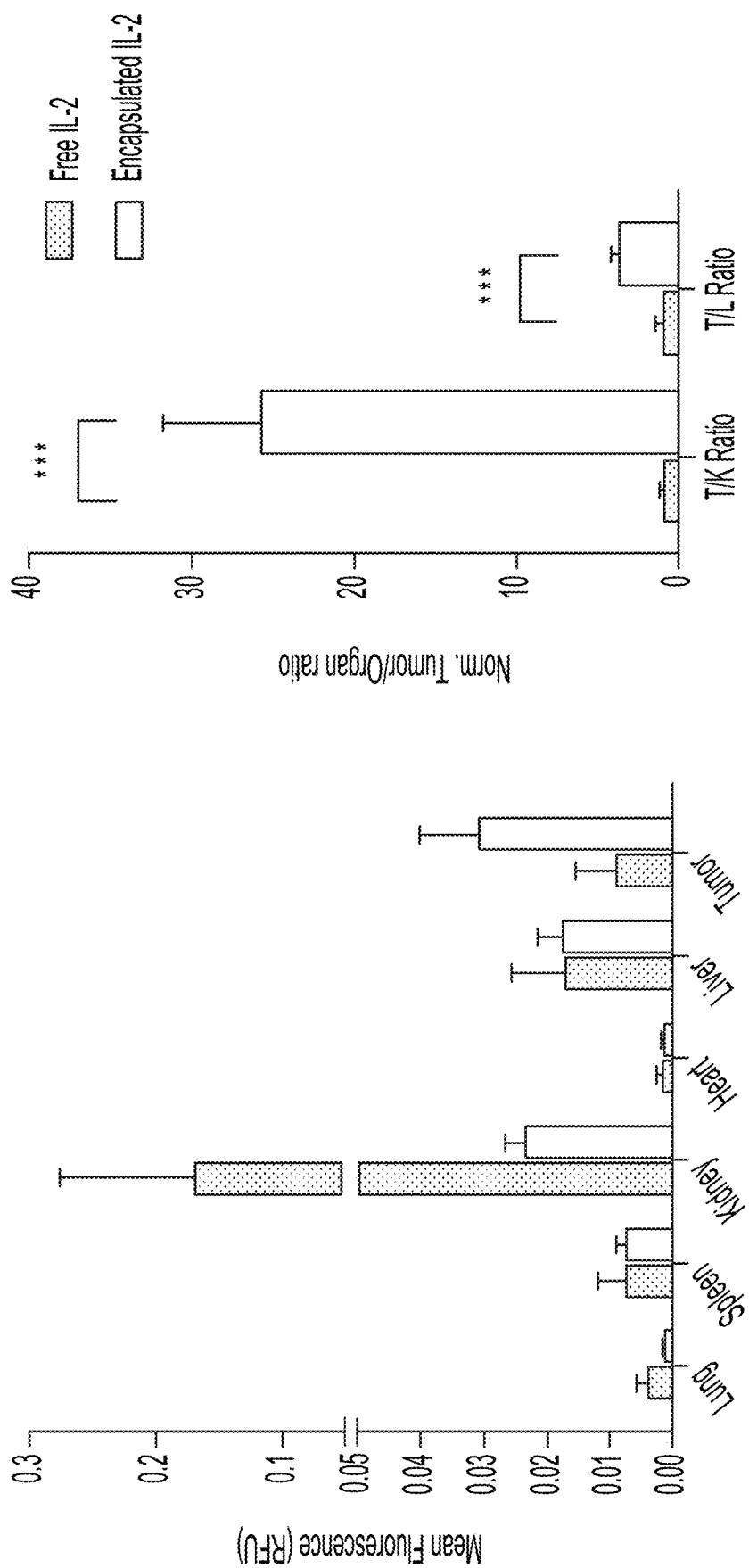

FIG. 17 shows that nanoparticles with different sized efficiently encapsulate IL-2 (800CW). WB for IL-2 with CST anti IL-2 Ab clone (D7A5) (1:4000 dilution) and Licor HRP-anti rabbit secondary (1:2000 dilution).

FIG. 18 shows that PDBA non-covalent formulations deliver IL-2 to head and neck orthotopic tumors in mice.

Figure 19:
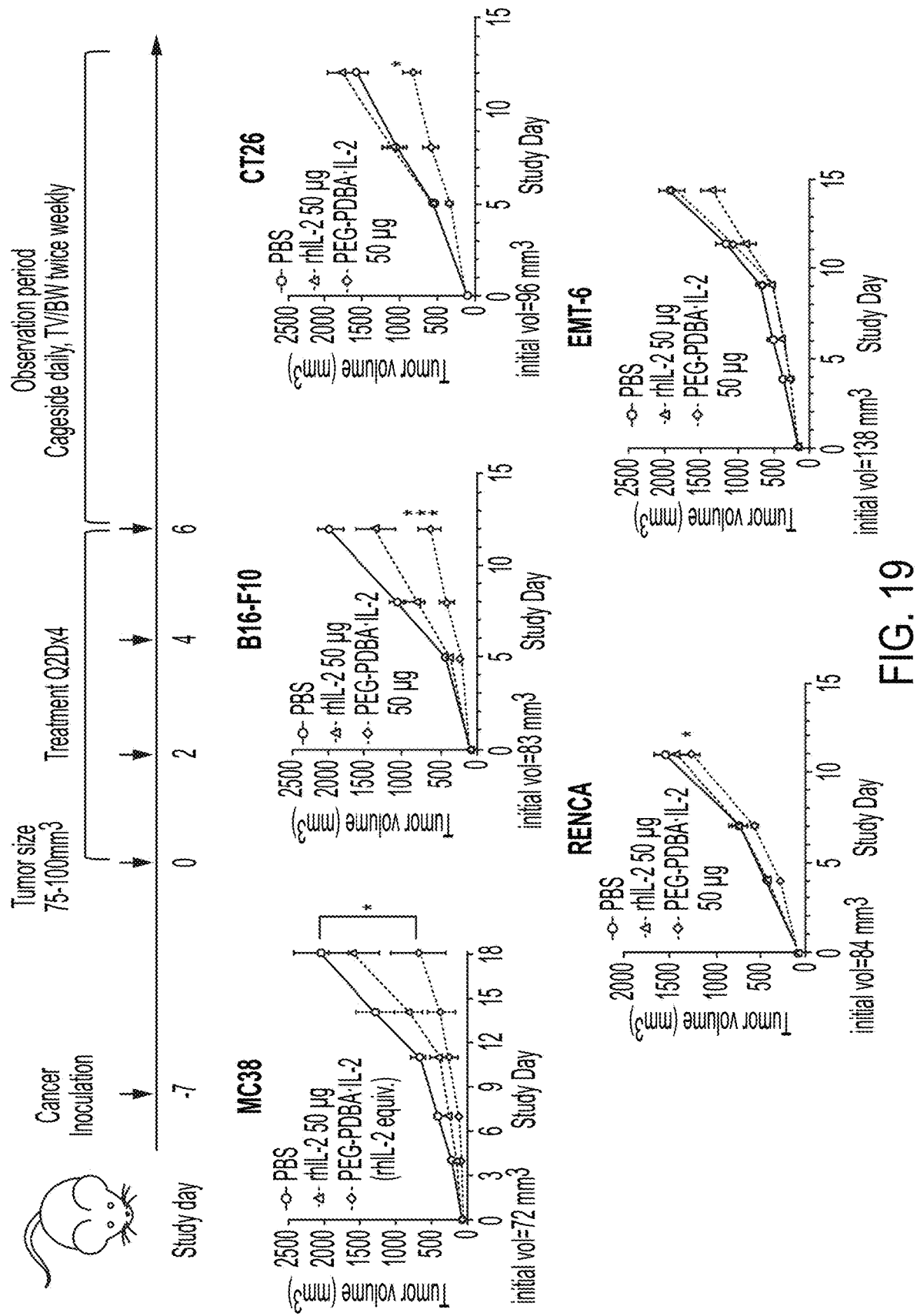

FIG. 19 shows that PDBA encapsulated IL-2 (800CW) inhibits cancer growth in multiple tumor models.

Figure 20A:
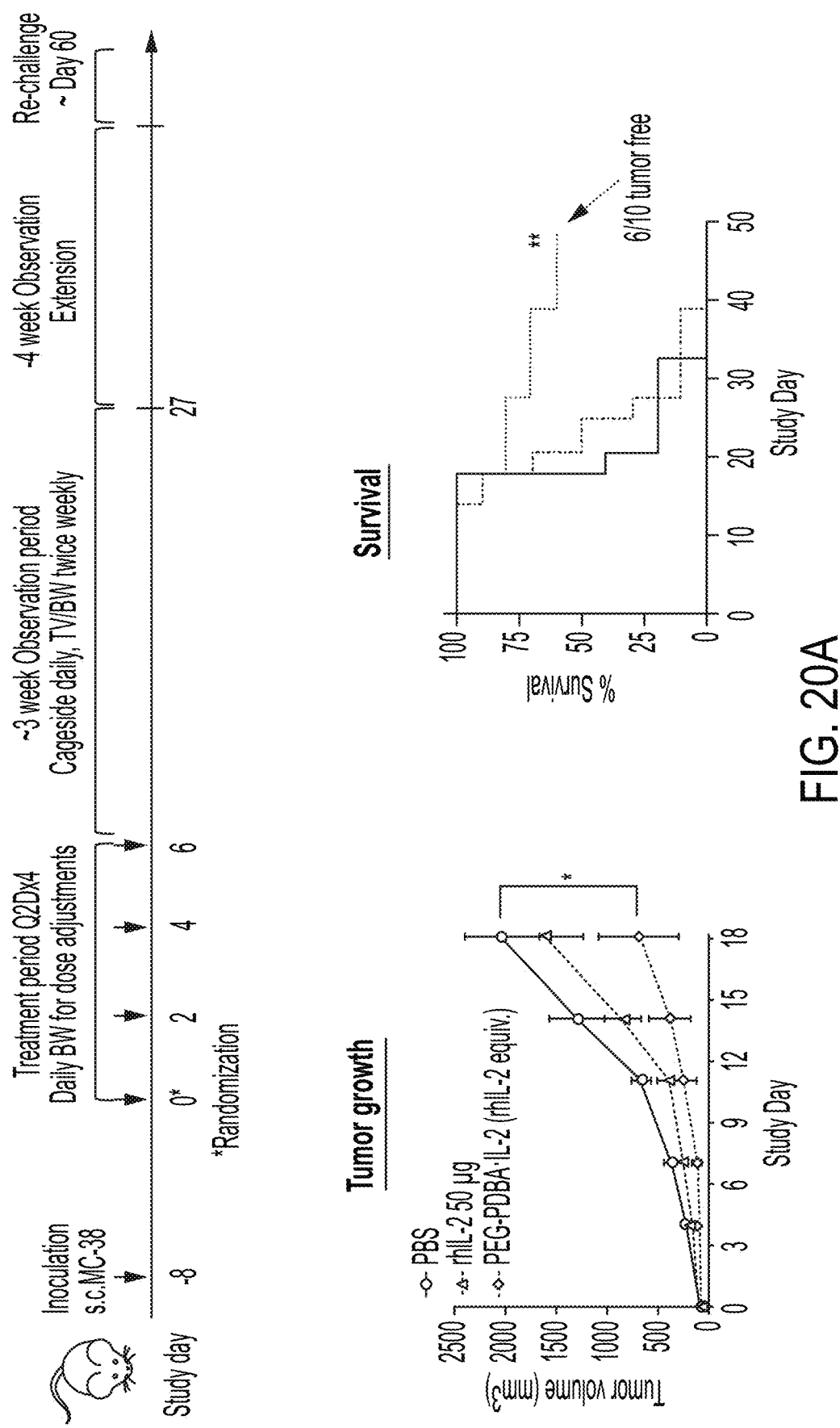
Figure 20B:
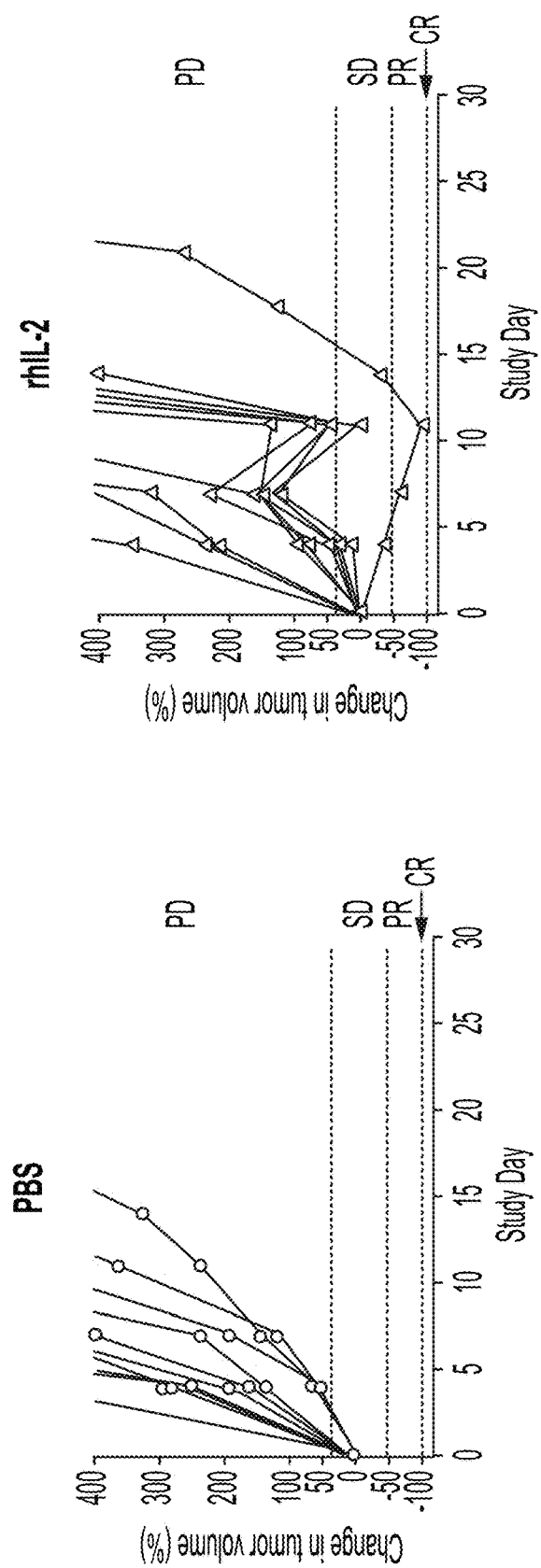
Figure 20C:
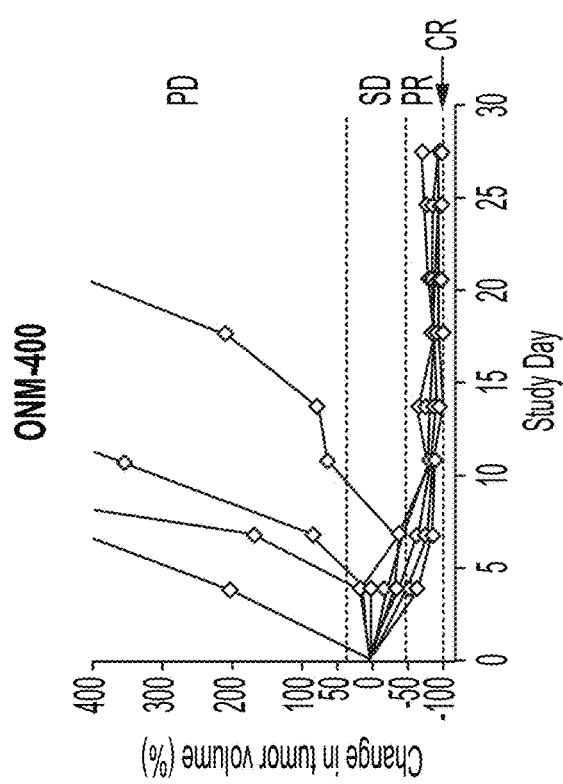

FIG. 20 shows PDBA encapsulated IL-2 (800CW) inhibits cancer growth and prolongs survival in animals.

Figure 21A:
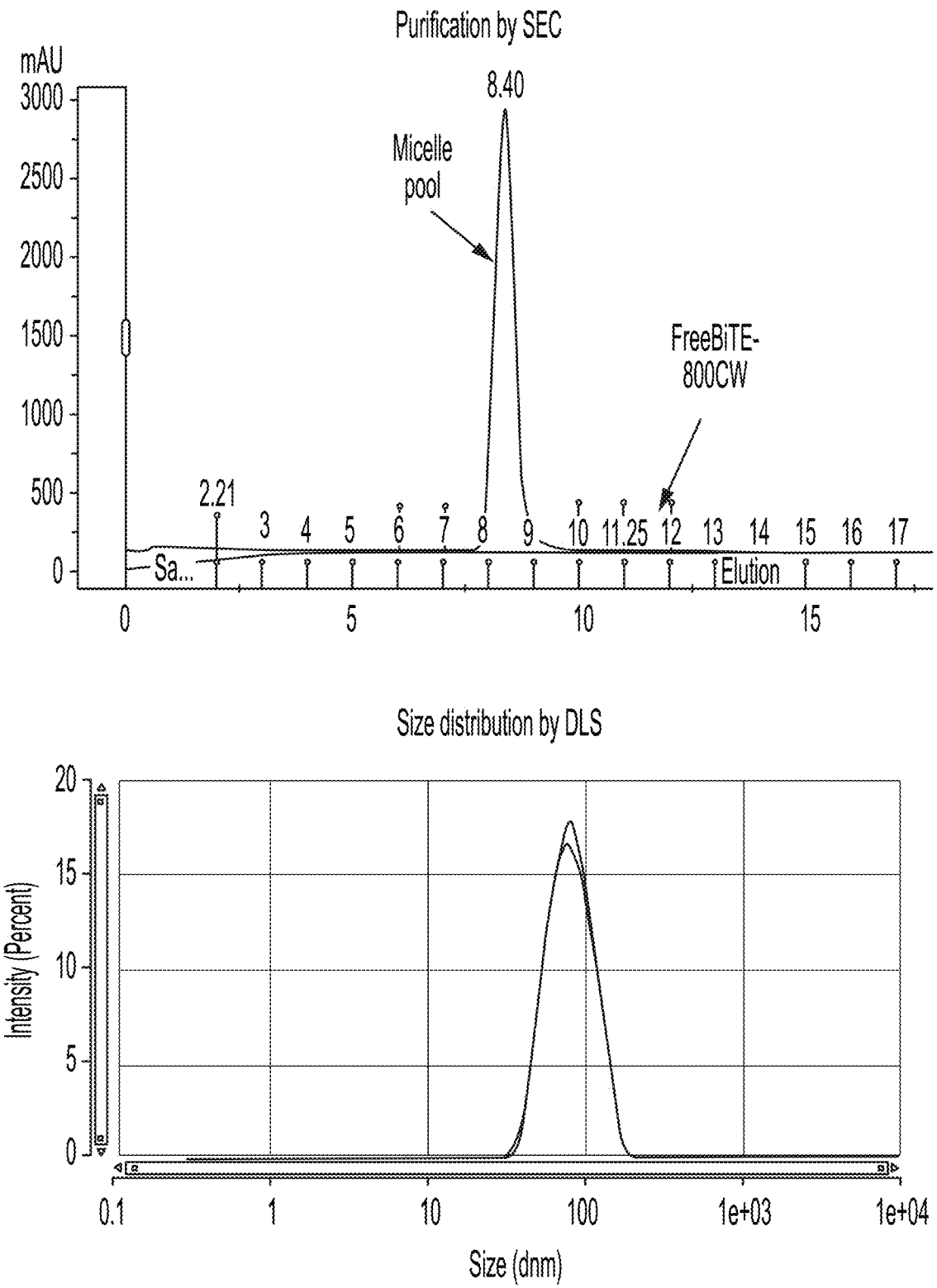
Figure 21B:

FIG. 21 shows that PDBA micelles successfully encapsulated 800CW modified bispecific antibody (BiTE).

Figure 22:
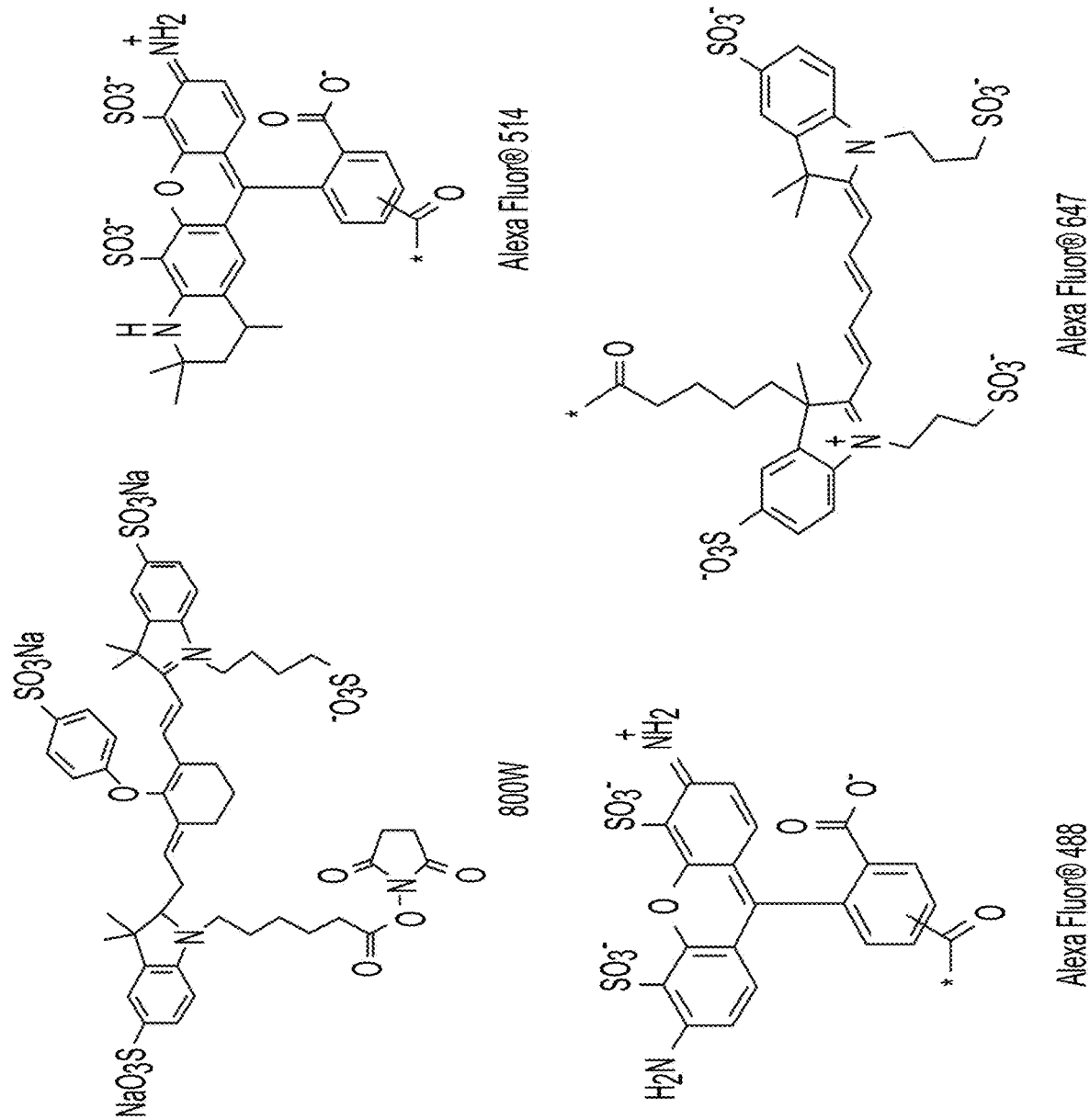

FIG. 22 shows the protein modification moieties.

Figure 23:
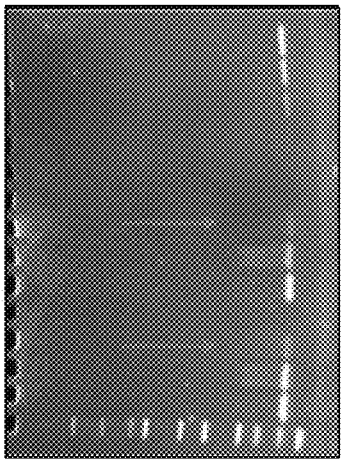
Figure 23:
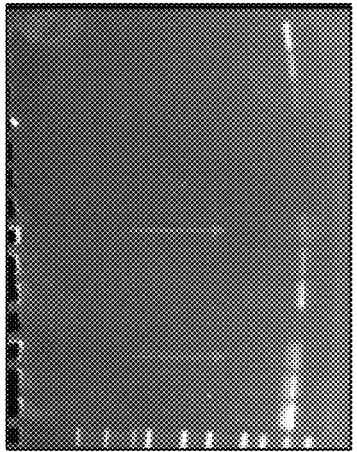

FIG. 23 shows Alexa® 488/515/647 or TME Modification of IL-2 can increase the loading with the pH-sensitive micelles.

DETAILED DESCRIPTION OF THE DISCLOSURE

Provided herein are block copolymers conjugated to a therapeutic agent. In other embodiments provided here in are micelle composition comprising a therapeutic agent.

I. Block Copolymers and Micelle Compositions

Micelles

One or more block copolymers described herein may be used to form a pH-sensitive micelle compositions. In some embodiments, the composition comprises a single type of micelle. In some embodiments, two or more different types of micelles may be combined to form a mixed-micelle composition. In some embodiments, the micelle comprises a block copolymer covalently conjugated to a therapeutic agent. In some embodiments, the micelle comprises one or more block copolymer that non-covalently encapsulates a therapeutic agent.

In an aspect, presented herein is a micelle comprising:
(i) a block copolymer having the structure of Formula (III), or a pharmaceutically acceptable salt, solvate, or hydrate thereof:

Formula (III)

wherein:
$n_3$ is an integer from 10-200;
$x_3$ is an integer from 40-300;
$y_3$ is an integer from 0-6;
$z_3$ is an integer from 0-10;

$X^3$ is a halogen, —OH, or —C(O)OH;

$R^8$ and $R^9$ are each independently an optionally substituted $C_1$-$C_6$ alkyl, $C_3$-$C_{10}$ cycloalkyl or aryl;

or $R^8$ and $R^9$ are taken together with the corresponding nitrogen to which they are attached to form an optionally substituted 5 to 7-membered ring;

each $R^{10}$ is independently hydrogen or ICG; and (ii) a therapeutic agent encapsulated by the block copolymer, wherein the therapeutic agent is a protein conjugated to a fluorescent dye.

In some embodiments of the micelle, the block copolymer of Formula (III) has the structure of Formula (III-c), or a pharmaceutically acceptable salt, solvate, or hydrate thereof:

Formula (III-c)

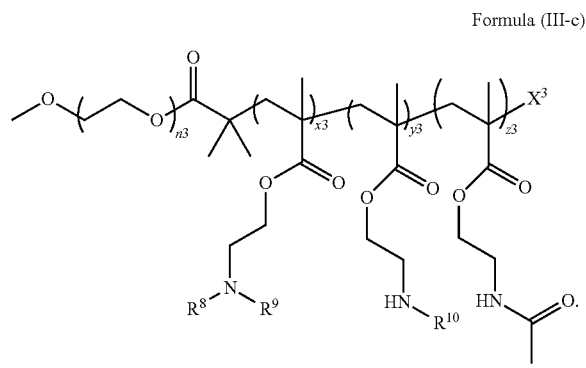

In some embodiments, $R^8$ and $R^9$ are the same group. In some embodiments, $R^8$ and $R^9$ are different groups.

In some embodiments, each $R^8$ and $R^9$ is independently an optionally substituted $C_1$-$C_6$ alkyl. In some embodiments, the alkyl is a straight chain or a branch alkyl. In some embodiments, the alkyl is a straight chain alkyl. In some embodiments, each $R^8$ and $R^9$ is independently —CH$_2$CH$_3$, —CH$_2$CH$_2$CH$_3$, or —CH$_2$CH$_2$CH$_2$CH$_3$. In some embodiments, each $R^8$ and $R^9$ is —CH$_2$CH$_2$CH$_2$CH$_3$. In some embodiments, each $R^8$ and $R^9$ is independently an optionally substituted $C_3$-$C_{10}$ cycloalkyl or aryl. In some embodiments, each $R^8$ and $R^9$ is independently an optionally substituted cyclopropyl, cyclobutyl, cyclopentyl, cyclohexyl, or cycloheptyl. In some embodiments, each $R^8$ and $R^9$ is independently an optionally substituted phenyl.

In some embodiments, $R^8$ and $R^8$ are taken together with the corresponding nitrogen to which they are attached to form an optionally substituted 5 to 7-membered ring. In some embodiments, $R^8$ and $R^9$ taken together are —CH$_2$(CH$_2$)$_2$CH$_2$—, —CH$_2$(CH$_2$)$_3$CH$_2$—, or —CH$_2$(CH$_2$)$_4$CH$_2$—. In some embodiments, $R^8$ and $R^9$ taken together are —CH$_2$(CH$_2$)$_4$CH$_2$—.

In some embodiments, $R^{10}$ is hydrogen. In some embodiments, $R^{10}$ is ICG.

The therapeutic agent may be incorporated into the micelles using methods known in the art. In some embodiments, the therapeutic agent is a protein. In some embodiments, the protein is a protein of about 5 to about 20 KDa, optionally a cytokine or fragment thereof, or is an antibody optionally an engineered antibody, or a fragment thereof. In some embodiments, the cytokine is an interleukin (IL), chemokine, interferon, lymphokine, monokine, colony stimulating factor, or tumor necrosis factor, optionally an IL-2, IL-1, IL-3, IL-4, IL-5, IL-6, IL-7, IL-8, IL-9, IL-10, IL-11, IL-12, IL-13, IL-15, IL-17, or IL-18 protein, or a fragment thereof. In some embodiments, the antibody or fragment thereof is a bispecific antibody or a fragment thereof or a fusion protein, optionally a bi-specific T-cell engager (BiTE).

In another aspect presented therein, is a micelle comprising:

(i) a block copolymer of Formula (IV), or a pharmaceutically acceptable salt, solvate, or hydrate thereof:

Formula (IV)

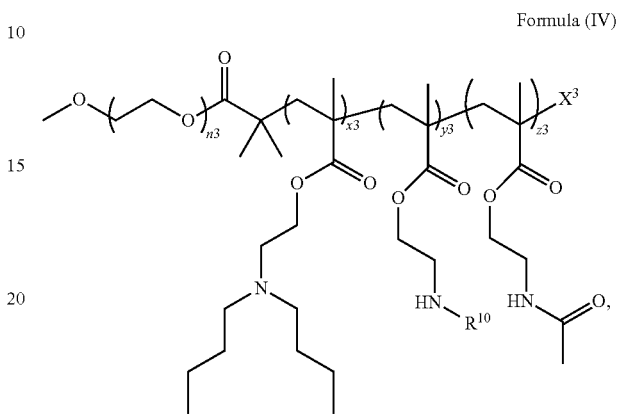

wherein:

$n_3$ is an integer from 10-200;

$x_3$ is an integer from 40-300;

$y_3$ is an integer from 0-6;

$z_3$ is an integer from 0-10;

each $R^{10}$ is independently hydrogen or ICG; and $X^3$ is a halogen, —OH, or —C(O)OH; and (ii) a therapeutic agents encapsulated by the block copolymer, wherein the therapeutic agent is a protein conjugated to a fluorescent dye.

In another aspect, presented herein is a micelle comprising:

(i) a block copolymer having the structure of Formula (III), or a pharmaceutically acceptable salt, solvate, or hydrate thereof:

Formula (III)

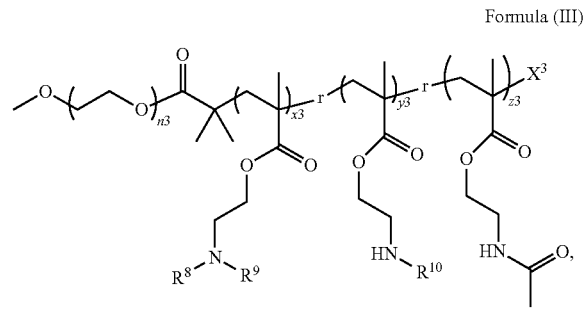

wherein:

$n_3$ is an integer from 10-200;

$x_3$ is an integer from 40-300;

$y_3$ is an integer from 0-6;

$z_3$ is an integer from 0-10;

$X^3$ is a halogen, —OH, or —C(O)OH;

$R^8$ and $R^9$ are each independently an optionally substituted $C_1$-$C_6$ alkyl, $C_3$-$C_{10}$ cycloalkyl or aryl;

or $R^8$ and $R^9$ are taken together with the corresponding nitrogen to which they are attached to form an optionally substituted 5 to 7-membered ring; and each R10 is independently hydrogen or ICG; and (ii) a block copolymer having the structure of Formula (I), or a pharmaceutically acceptable salt, solvate, or hydrate thereof:

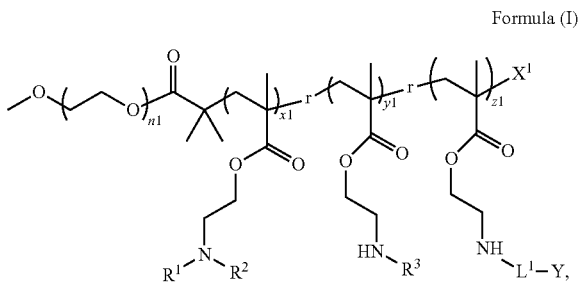

Formula (I)

wherein:
n1 is an integer from 10-200;
x1 is an integer from 40-300;
y1 is an integer from 0-6;
z1 is an integer from 0-10;
X1 is a halogen, —OH, or —C(O)OH;
R1 and R2 are each independently an optionally substituted C1-C6 alkyl, C3-C10 cycloalkyl or aryl;
or R1 and R2 are taken together with the corresponding nitrogen to which they are attached to form an optionally substituted 5 to 7-membered ring;
each R3 is independently hydrogen, acyl, or ICG;
L1 is a bond or —C(O)—, or optionally substituted C1-C10 linker or PEG linker, wherein each is optionally substituted with a maleimide residual;
Y is a therapeutic agent; or (ii) a block copolymer having the structure of Formula (II), or a pharmaceutically acceptable salt, solvate, or hydrate thereof:

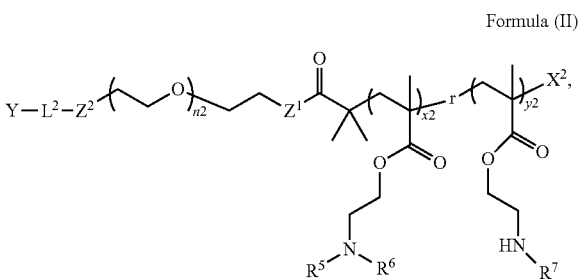

Formula (II)

wherein:
n2 is an integer from 2-200;
x2 is an integer from 40-300;
y2 is an integer from 0-6;
X2 is a halogen, —OH, or —C(O)OH;
R5 and R6 are each independently an optionally substituted C1-C6 alkyl, C3-C10 cycloalkyl or aryl;
or R5 and R6 are taken together with the corresponding nitrogen to which they are attached to form an optionally substituted 5 to 7-membered ring;
each R7 is independently hydrogen, acyl, or ICG;
Z1 is —NH— or —O—;
Z2 is —NH—, —O—, or a substituted triazole;

L2 is a bond or —C(O)—, or optionally substituted C1-C10 linker or PEG linker, wherein each is optionally substituted with a maleimide residual; and
Y is a therapeutic agent.

In another aspect, is a micelle comprising:

(i) a block copolymer having the structure of Formula (III), or a pharmaceutically acceptable salt, solvate, or hydrate thereof:

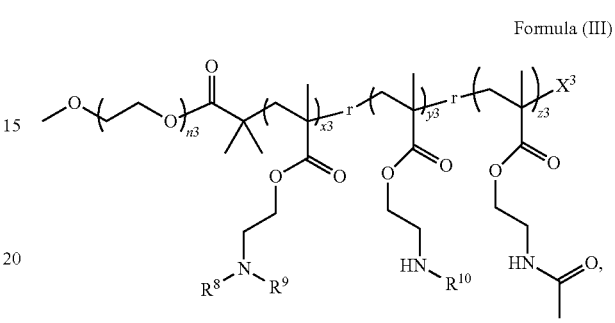

Formula (III)

wherein:
n3 is an integer from 10-200;
x3 is an integer from 40-300;
y3 is an integer from 0-6;
z3 is an integer from 0-10;
X3 is a halogen, —OH, or C(O)OH;
R8 and R9 are each independently an optionally substituted C1-C6 alkyl, C3-C10 cycloalkyl or aryl; and
or R8 and R9 are taken together with the corresponding nitrogen to which they are attached to form an optionally substituted 5 to 7-membered ring; and
each R10 is independently hydrogen or ICG;

(ii) a block copolymer having the structure of Formula (I), or a pharmaceutically acceptable salt, solvate, or hydrate thereof:

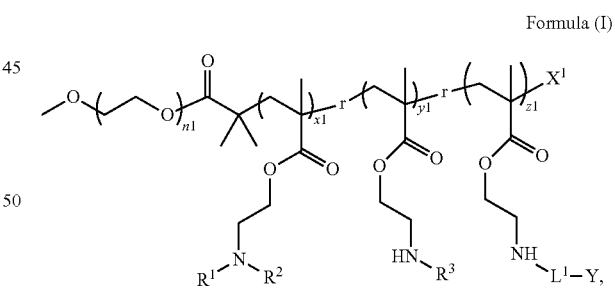

Formula (I)

wherein:
n1 is an integer from 10-200;
x1 is an integer from 40-300;
y1 is an integer from 0-6;
z1 is an integer from 0-10;
X1 is a halogen, —OH, or —C(O)OH;
R1 and R2 are each independently an optionally substituted C1-C6 alkyl, C3-C10 cycloalkyl or aryl;
or R1 and R2 are taken together with the corresponding nitrogen to which they are attached to form an optionally substituted 5 to 7-membered ring;

each R3 is independently hydrogen, acyl, or ICG;
L1 is a bond or —C(O)—, or optionally substituted C1-C10 alkylene linker or PEG linker, wherein each is optionally substituted with a maleimide residual; and
Y is a therapeutic agent; and (iii) a block copolymer having the structure of Formula (II), or a pharmaceutically acceptable salt, solvate, or hydrate thereof:

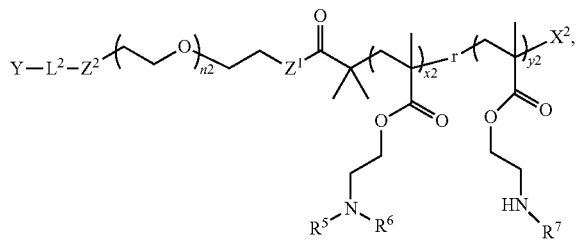

Formula (II)

wherein:
n2 is an integer from 2-200;
x2 is an integer from 40-300;
y2 is an integer from 0-6;
X2 is a halogen, —OH, or —C(O)OH;
R5 and R6 are each independently an optionally substituted C1-C6 alkyl, C3-C10 cycloalkyl or aryl;
or R5 and R6 are taken together with the corresponding nitrogen to which they are attached to form an optionally substituted 5 to 7-membered ring;
each R7 is independently hydrogen, acyl, or ICG;
Z1 is —NH— or —O—;
Z2 is —NH—, —O—, or a substituted triazole residual;
L2 is a bond or —C(O)—, or optionally substituted C1-C10 alkylene linker or PEG linker, wherein each is optionally substituted with a maleimide residual; and
Y is a therapeutic agent.

In some embodiments of Formula (I), $R^1$ and $R^2$ are the same group. In some embodiments, $R^1$ and $R^2$ are different groups.

In some embodiments, each $R^1$ and $R^2$ is independently an optionally substituted $C_1$-$C_6$ alkyl. In some embodiments, the alkyl is a straight chain or a branch alkyl. In some embodiments, the alkyl is a straight chain alkyl. In some embodiments, each $R^1$ and $R^2$ is independently —$CH_2CH_3$, —$CH_2CH_2CH_3$, or —$CH_2CH_2CH_2CH_3$. In some embodiments, each $R^1$ and $R^2$ is —$CH_2CH_2CH_2CH_3$.

In some embodiments, each $R^1$ and $R^2$ are each independently an optionally substituted $C_3$-$C_{10}$ cycloalkyl or aryl. In some embodiments, each $R^1$ and $R^2$ is independently an optionally substituted cyclopropyl, cyclobutyl, cyclopentyl, cyclohexyl, or cycloheptyl. In some embodiments, each $R^1$ and $R^2$ is independently an optionally substituted phenyl.

In some embodiments, $R^1$ and $R^2$ are taken together with the corresponding nitrogen to which they are attached to form an optionally substituted 5 to 7-membered ring. In some embodiments, $R^1$ and $R^2$ taken together are —$CH_2(CH_2)_2CH_2$—, —$CH_2(CH_2)_3CH_2$—, or —$CH_2(CH_2)_4CH_2$—. In some embodiments, $R^1$ and $R^2$ taken together is —$CH_2(CH_2)_4CH_2$—.

In some embodiments, each $R^3$ is independently acyl or ICG. In some embodiments, each $R^3$ is independently acyl. In some embodiments, each $R^3$ is independently ICG. In some embodiments, each $R^3$ is independently hydrogen.

In some embodiments, $L^1$ an optionally substituted bifunctional linker capable of binding to the block copolymer and to a therapeutic agent. In some embodiments, $L^1$ is an optionally substituted $C_1$-$C_{10}$ alkylene linker, optionally substituted with maleimide residual. In some embodiments, $L^1$ is an optionally substituted PEG linker, optionally substituted with a maleimide residual.

In some embodiments, $L^1$ is

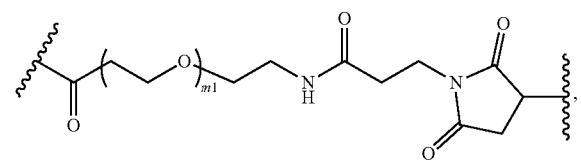

wherein $m_1$ is an integer from 2-20 or any integer therein.

In some embodiments, the block copolymer of Formula (I) has the structure of Formula (I-a), or a pharmaceutically acceptable salt or solvate thereof:

Formula (I-a)

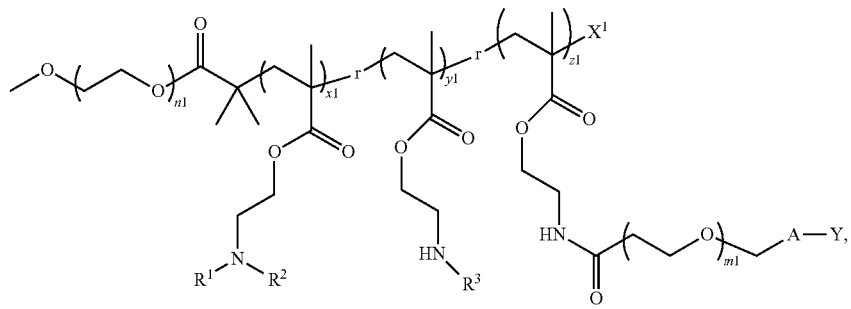

wherein:
m1 is an integer from 2-200; and
A is a bond or —C(O)— optionally substituted with a maleimide residual.

In some embodiments of the block copolymer of Formula (I) or (I-a), $m_1$ is an integer from 2-20 or any integer therein. In some embodiments of the block copolymer of Formula (I) or (I-a), $m_1$ is an integer from 2-5, 6-9, 10-14, or 15-20, or any integer therein.

In some embodiments of the block copolymer of Formula (I) or (I-a), A is a bond. In some embodiments, A is —C(O)— optionally substituted with a maleimide residual.

In some embodiments, the block copolymer of Formula (I) has the structure of Formula (I-c), or a pharmaceutically acceptable salt, solvate, or hydrate thereof:

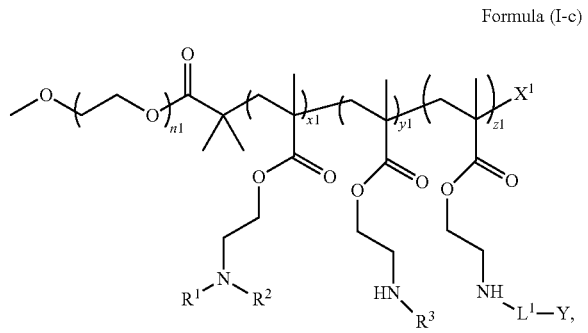

Formula (I-c)

In some embodiments of Formula (II), $R^5$ and $R^6$ are the same group. In some embodiments, $R^5$ and $R^6$ are different groups.

In some embodiments, each $R^5$ and $R^6$ is independently an optionally substituted $C_1$-$C_6$ alkyl. In some embodiments, the alkyl is a straight chain or a branch alkyl. In some embodiments, the alkyl is a straight chain alkyl. In some embodiments, each $R^5$ and $R^6$ is independently —$CH_2CH_3$, —$CH_2CH_2CH_3$, or —$CH_2CH_2CH_2CH_3$. In some embodiments, each $R^5$ and $R^6$ is —$CH_2CH_2CH_2CH_3$.

In some embodiments, each $R^5$ and $R^6$ is independently an optionally substituted $C_3$-$C_{10}$ cycloalkyl or aryl. In some embodiments, each $R^5$ and $R^6$ is independently an optionally substituted cyclopropyl, cyclobutyl, cyclopentyl, cyclohexyl, or cycloheptyl. In some embodiments, each $R^5$ and $R^6$ is independently an optionally substituted phenyl.

In some embodiments, $R^5$ and $R^6$ are taken together with the corresponding nitrogen to which they are attached to form an optionally substituted 5 to 7-membered ring. In some embodiments, $R^5$ and $R^6$ taken together are —$CH_2(CH_2)_2CH_2$—, —$CH_2(CH_2)_3CH_2$—, or —$CH_2(CH_2)_4CH_2$—.

In some embodiments, each $R^7$ is independently acyl or ICG. In some embodiments, each $R^7$ is independently acyl. In some embodiments, each $R^7$ is independently ICG. In some embodiments, each $R^7$ is independently hydrogen.

In some embodiments, $Z^1$ is —O—. In some embodiments, $Z^1$ is —NH—.

In some embodiments, $Z^2$ is —NH— or —O—. In some embodiments, $Z^2$ is —O—. In some embodiments, $Z^2$ is —NH—. In some embodiments, $Z^2$ is a substituted triazole.

In some embodiments, $L^2$ an optionally substituted bifunctional linker capable of binding to the block copolymer and to a therapeutic agent. In some embodiments, $L^2$ is an optionally substituted $C_1$-$C_{10}$ alkylene linker, optionally substituted with maleimide residual. In some embodiments, $L^2$ is an optionally substituted PEG linker, optionally substituted with a maleimide residual. In some embodiments, $L^2$ is

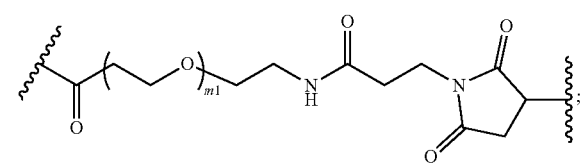

wherein $m_2$ is 2-200.

In some embodiments, the block copolymer of Formula (II) has the structure of Formula (II-a), or a pharmaceutically acceptable salt or solvate thereof:

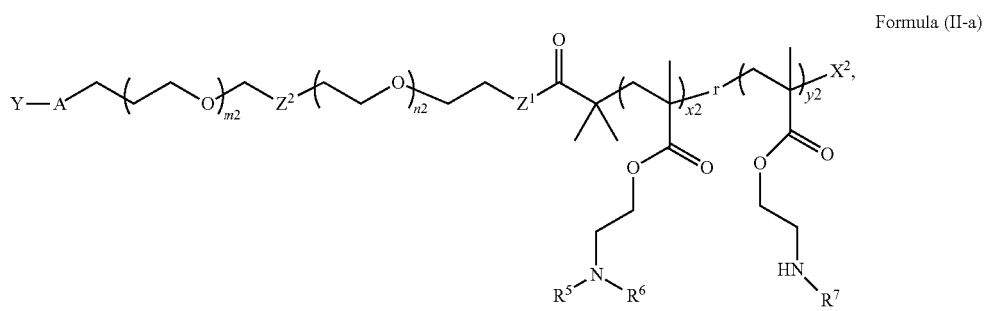

Formula (II-a)

wherein:
  m2 is 2-200; and
  A is a bond or —C(O)— optionally substituted with a maleimide residual.

In some embodiments of the block copolymer of Formula (II) or (II-a), $m_2$ is an integer from 2-20. In some embodiments of the block copolymer of Formula (II) or (II-a), $m_2$ is an integer from 2-5, 6-9, 10-14, or 15-20, or any integer therein.

In some embodiments of the block copolymer of Formula (II) or (II-a), A is a bond. In some embodiments, A is —C(O)— optionally substituted with a maleimide residual.

In some embodiments, the block copolymer of Formula (II) has the structure of Formula (II-c), or a pharmaceutically acceptable salt, solvate, or hydrate thereof:

Formula (II-c)

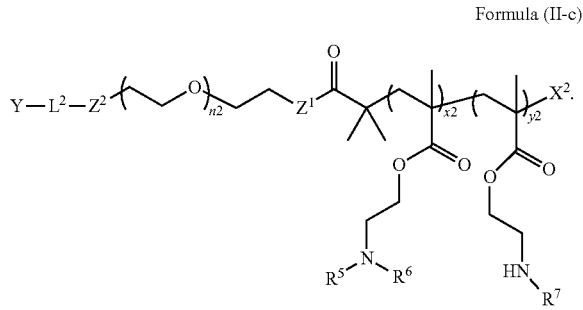

In some embodiments, the block copolymer of Formula (II) has the structure of Formula (II-a2), or a pharmaceutically acceptable salt or solvate thereof:

Formula (II-a2)

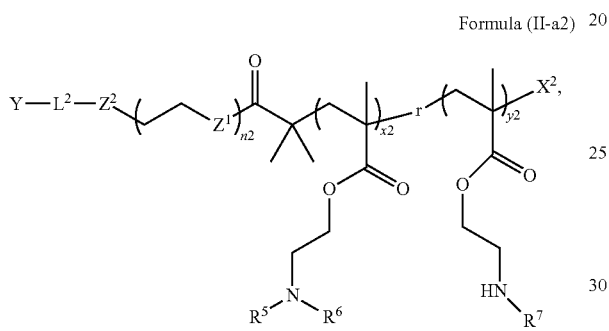

wherein:
Z1 is —O—.

In some embodiments, the protein is a protein of about 5 to about 20 KDa, optionally a cytokine or fragment thereof, or is an antibody optionally an engineered antibody, or a fragment thereof. In some embodiments, the cytokine is an interleukin (IL), chemokine, interferon, lymphokine, monokine, colony stimulating factor, or tumor necrosis factor, optionally an IL-2, IL-1, IL-3, IL-4, IL-5, IL-6, IL-7, IL-8, IL-9, IL-10, IL-11, IL-12, IL-13, IL-15, IL-17, or IL-18 protein, or a fragment thereof. In some embodiments, the antibody or fragment thereof is a bispecific antibody or a fragment thereof or a fusion protein, optionally a bi-specific T-cell engager (BiTE).

Block Copolymers

In some embodiments, the block copolymer is a diblock copolymer. In some embodiments, the block copolymer comprises a hydrophilic polymer segment and a hydrophobic polymer segment. In some embodiments, the hydrophilic polymer segment comprises poly(ethylene oxide) (PEO). In some embodiments, the hydrophilic polymer segment is about 2 kD to about 10 kD in size. In some embodiments, the hydrophilic polymer segment is about 2 kD to about 5 kD in size. In some embodiments, the hydrophilic polymer segment is about 3 kD to about 8 kD in size. In some embodiments, the hydrophilic polymer segment is about 4 kD to about 6 kD in size. In some embodiments, the hydrophilic polymer segment is about 5 kD in size.

In some embodiments, each $n_1$, $n_2$, and $n_3$ is independently an integer from 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99, 100-109, 110-119, 120-129, 130-139, 140-149, 150-159, 160-169, 170-179, 180-189, 190-199 or any range derivable therein. In some embodiments, each $n_1$, $n_2$, and $n_3$ is independently an integer from 60-150, 100-140, or 110-120. In some embodiments, each $n_1$, $n_2$, and $n_3$ is independently 100-140.

In some embodiments, the block copolymer comprises a hydrophobic polymer segment. In some embodiments, the hydrophobic polymer segment comprises a tertiary amine. In some embodiments, the hydrophobic polymer segment is selected from:

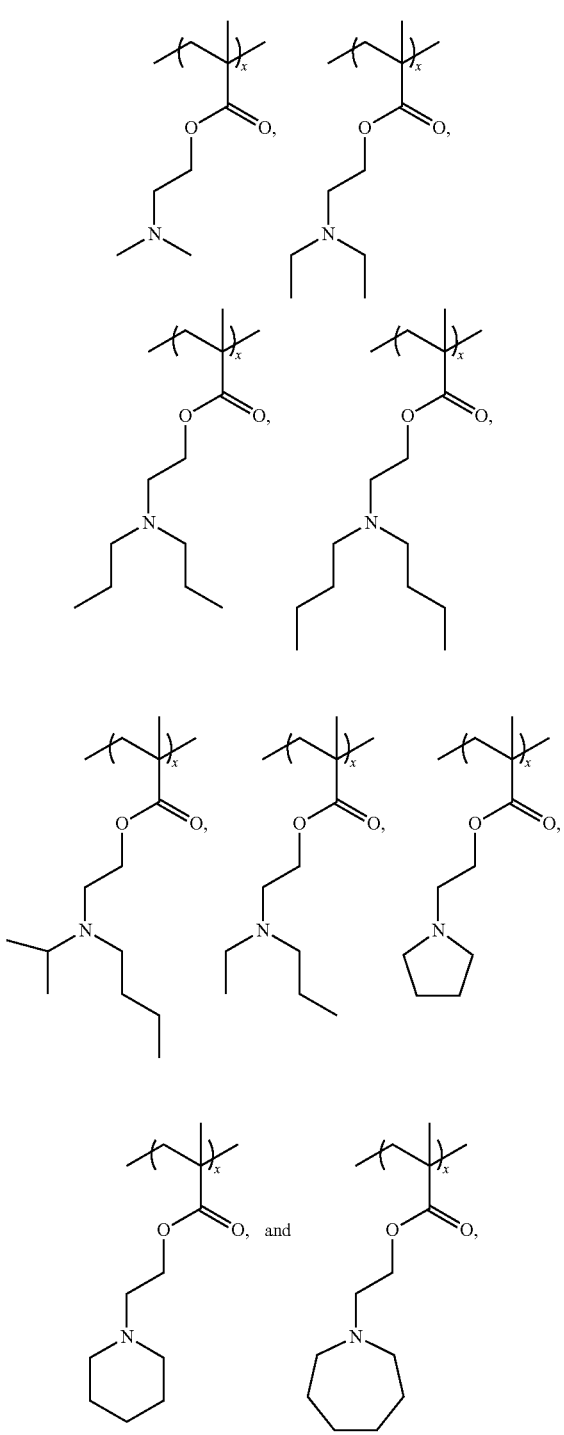

wherein x is about 40-300 in total.

In some embodiments, the hydrophobic segment comprises a dibutyl amine. In some embodiments, the hydrophobic segment comprises

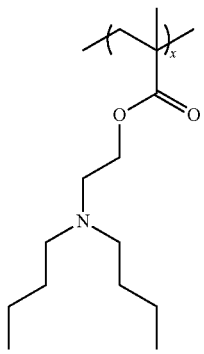

In some embodiments, each $x_1$, $x_2$, and $x_3$ is independently an integer 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99, 100-109, 110-119, 120-129, 130-139, 140-149, 150-159, 160-169, 170-179, 180-189, 190-199 or any range derivable therein. In some embodiments, each $x_1$, $x_2$, and $x_3$ is independently an integer from 50-200, 60-160, or 90-140. In some embodiments, each $x_1$, $x_2$, and $x_3$ is independently 90-140.

In some embodiments, each $y_1$, $y_2$, and $y_3$ is independently an integer from 1-6, 1-5, 1-4, or 1-3, or any range derivable therein. In some embodiments, each $y_1$, $y_2$, and $y_3$ is independently 1, 2, 3, 4, 5, or 6. In some embodiments, each $y_1$, $y_2$, and $y_3$ is independently 0.

In some embodiments, each $z_1$ and $z_2$ is independently an integer from 1-9, 1-8, 1-7, 1-6, 1-5, 1-4, or 1-3, or any range derivable therein. In some embodiments, each $z_1$ and $z_2$ is independently 1, 2, 3, 4, 5, 6, 7, 8, 9, or 10. In some embodiments, each $z_1$ and $z_2$ is independently 0.

The term "r" denotes a connection between different block copolymer units/segments (e.g., represented by $x_1$, $y_1$, and $z_1$). In some embodiments, each r is independently a bond connecting carbon atoms of the units/segments, or an alkyl group —$(CH_2)n$- wherein n is 1 to 10 In some embodiments, the copolymer block segments/units (e.g., represented by $x_1$, $y_1$, and $z_1$) can occur in any order, sequence, or configuration. In some embodiments, the copolymer block units occur sequentially as described in Formulas (I), (I-a), (I-c), (II), (II-a), (II-c), (III), or (IV).

In some embodiments, each $m_1$ and $m_2$ is independently an integer from 2-200. In some embodiments, each $m_1$ and $m_2$ is independently an integer from 2-20.

In some embodiments, each $X^1$, $X^2$, and $X^3$ is a terminal group. In some embodiments, the terminal capping group is the product of an atom transfer radical polymerization (ATRP) reaction. For example, the terminal capping group may be a halogen, such as —Br, when atom transfer radical polymerization (ATRP) is used. In some embodiments, each $X^1$, $X^2$, and $X^3$ is independently Br. In some embodiments, each $X^1$, $X^2$, and $X^3$ is independently —OH. In some embodiments, each $X^1$, $X^2$, and $X^3$ is independently an acid. In some embodiments, each $X^1$, $X^2$, and $X^3$ is independently —C(O)OH. In some embodiments, each $X^1$, $X^2$, and $X^3$ is independently H. The end group may optionally be further modified following polymerization with an appropriate moiety.

In some embodiments, the linker $L^1$ and $L^2$ is a bifunctional linker with groups that react with the block copolymer and the therapeutic agent. In some embodiments, the linker is component used is maleimide-PEG-NHS, NHS-carbonate (N-hydroxysuccinimide carbonate), SPDB (N-succinimidyl-4-(2-pyridyldithio)butanoate), or CDI (carbonyldiimidazole).

In some embodiments, the linker is conjugated to a therapeutic agent. In some embodiments, the linker is covalently conjugated to a therapeutic agent. Methods known in the art may be used to conjugate the therapeutic agent to, for example the hydrophobic polymer segment.

In some embodiments, the block copolymer comprises a fluorescent dye conjugated through an amine. In some embodiments, the fluorescent dye is a cyanine dye or a derivative thereof. In some embodiments, the fluorescent dye is indocyanine green (ICG) or a derivative thereof. Indocyanine green (ICG) is used in medical diagnostics. In some embodiments, the structure of the ICG derivative is:

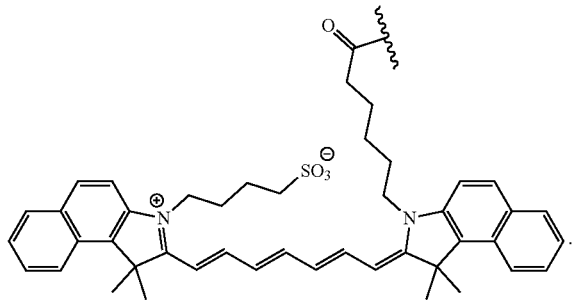

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

Therapeutic Agents

In some embodiments, the therapeutic agent is a protein. In some embodiments, the protein is a protein of about 5 to about 20 KDa optionally a cytokine or fragment thereof, or is an antibody optionally an engineered antibody, or a fragment thereof. In some embodiments, the therapeutic agent is a cytokine or fragment thereof or an engineered antibody fragment.

In some embodiments, the therapeutic agent is a cytokine of a fragment thereof. Cytokines are a broad and loose category of small proteins that are important in cell signaling. Cytokines are peptides and cannot cross the lipid bilayer of cells to enter the cytoplasm. Cytokines have been shown to be involved in autocrine, paracrine and endocrine signaling as immunomodulating agents. Interleukin-2 (IL-2) is an interleukin, a type of cytokine signaling molecule in the immune system. It is a 15.5-16 kDa protein that regulates the activities of white blood cells that are responsible for immunity. Interleukin-15 (IL-15) is a cytokine with structural similarity to Interleukin-2. Like IL-2, IL-15 binds to and signals through a complex composed of IL-2/IL-15 receptor beta chain and the common gamma chain. IL-15 is secreted by mononuclear phagocytes following infection by virus. Interleukin-21 is a cytokine that has potent regulatory effects on cells of the immune system, including natural killer cells and cytotoxic T cells that can destroy virally infected or cancerous cells. Interleukin 12 (IL-12) is an interleukin that is naturally produced by dendritic cells, macrophages, neutrophils, and human B-lymphoblastoid cells (NC-37) in response to antigenic stimulation. In some embodiments, the cytokine is an interleukin (IL), chemokine, interferon, lymphokine, monokine, colony stimulating factor, or tumor necrosis factor, optionally an IL-2, IL-1, IL-3, IL-4, IL-5, IL-6, IL-7, IL-8, IL-9, IL-10, IL-11, IL-12, IL-13, IL-15, IL-17, or IL-18 protein, or a fragment thereof. In some embodiments, the cytokine is IL-2, IL-21, IL-12 or IL-15 or a fragment thereof. In some embodiments, the cytokine is IL-2, IL-12, or IL-15 or a fragment thereof. In some embodiments, the cytokine is IL-2 or a fragment thereof. In some embodiments, the cytokine is IL-15 or a fragment thereof. In some embodiments, the cytokine is IL-12 or a fragment thereof. In some embodiments, the cytokine is Fab or a fragment thereof.

Interferons (IFNs) are a group of signaling proteins that belong to the class of proteins known as cytokines, molecules used for communication between cells to trigger the protective defenses of the immune system that help eradicate pathogens. In some embodiments, the cytokine is interferon α, interferon β, or interferon γ or a fragment thereof.

Granulocyte-macrophage colony-stimulating factor, also known as colony-stimulating factor 2, is a monomeric glycoprotein secreted by macrophages, T cells, mast cells, natural killer cells, endothelial cells and fibroblasts that functions as a cytokine. In some embodiments, the cytokine is gramlocyte-macrophage colony-stimulating factor GM-CSF.

In some embodiments, the therapeutic agent is an engineered antibody fragment. In some embodiments, the engineered antibody fragment is a bi-specific T cell engager. Bi-specific T-cell engagers (BiTE) are a class of artificial bispecific monoclonal antibodies that are investigated for the use as anti-cancer drugs. They direct a host's immune system, more specifically the T cells' cytotoxic activity, against cancer cells. In some embodiments, the antibody or fragment thereof is a bispecific antibody or a fragment thereof or a fusion protein, optionally a bi-specific T-cell engager (BiTE).

Protein Modification

In certain embodiments, the therapeutic agent is conjugated to a fluorescent dye. In some embodiments, the therapeutic agent is conjugated to a fluorescent dye prior to encapsulation by the block copolymer.

In some embodiments, the fluorescent dye has an excitation spectrum from about 400 nm to about 900 nm, or about: 400, 450, 500, 550, 600, 650, 700, 750, 800, or 850 nm.

In some embodiments, the fluorescent dye is coumarin, rhodamine, cyanine, xanthene, fluorescein, or a sulfonated or negatively charged form thereof, or a compound from FIG. 22.

In some embodiments, the fluorescent dye is 800CW, Alexa Fluor®514, Alexa Fluor®488, or Alexa Fluor®647. In some embodiments, the fluorescent dye is 800CW. In some embodiments, the fluorescent dye is a compound from FIG. 22.

In some embodiments, the fluorescent dye is:

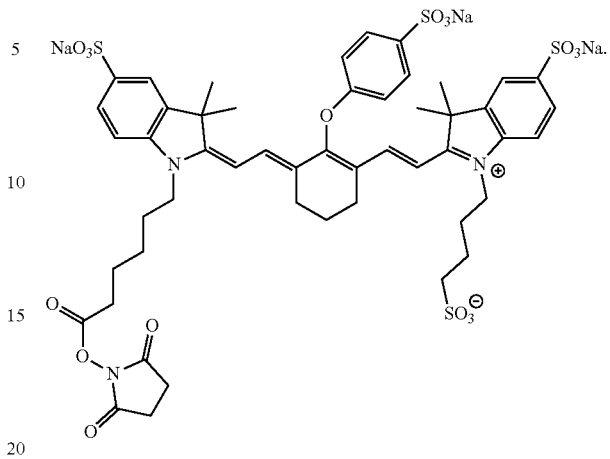

Micelle Compositions

In some embodiments, the micelle comprises one or more different types of block copolymer components from various unimers. In some embodiments, the micelle comprises (i) a block copolymer of Formula (III) and (ii) a block copolymer of Formula (I) or Formula (II). In some embodiments, the micelle comprises a ratio from 1:99 to 99:1 of components (i) to (ii); or any ratio therein. In some embodiments, the micelle comprises a ratio from 1:99, 10:90, 20:80, 30:70, 40:50 or 50:50 of components (i) and (ii). In some embodiments, the micelle comprises a 1:1 ratio of components (i) and (ii).

In some embodiments, the micelle comprises a 1:99 of the block copolymer of Formula (III) to the block copolymer of Formula (I). In some embodiments, the micelle comprises 99:1 of the block copolymer of Formula (III) to the block copolymer of Formula (I). In some embodiments, the micelle comprises 1:99 of the block copolymer of Formula (III) to the block copolymer of Formula (II). In some embodiments, the micelle comprises 99:1 of the block copolymer of Formula (III) to the block copolymer of Formula (II).

In some embodiments, the micelle comprises (i) a block copolymer of Formula (III); (ii) a block copolymer of Formula (I); and (iii) a block copolymer of Formula (II). In some embodiments, the micelle comprises equal part of components (i), (ii), and (iii). In some embodiments, the micelle comprises unequal part of components (i), (ii), and (iii).

In some embodiments, each different type of block copolymer is conjugated to a different therapeutic agent. In some embodiments, each different type of block copolymer is conjugated to the same therapeutic agent.

In another aspect presented herein is a micelle, comprising: (i) a block copolymer of Formula (III); (ii) a block copolymer of Formula (I) and/or a block copolymer of Formula (II); and (iii) a therapeutic agent non-covalently encapsulated by the block copolymers. In some embodiments, the therapeutic agent is non-covalently encapsulated within the micelle.

The use of micelles in cancer therapy may enhance anti-tumor efficacy and reduce toxicity to healthy tissues, in part due to the size of the micelles. While small molecules such as certain chemotherapeutic agents can enter both normal and tumor tissues, non-targeted micelle nanoparticles may preferentially cross leaky tumor vasculature. The size of the micelles will typically be in the nanometer scale (i.e., between about 1 nm and 1 μm in diameter). In some embodiments, the micelle has a size of about 10 to about 200 nm. In some embodiments, the micelle has a size of about 20 to about 100 nm. In some embodiments, the micelle has a size of about 30 to about 50 nm. In some embodiments, the micelle has a diameter less than about 1 μm. In some embodiments, the micelle has a diameter less than about 100 nm. In some embodiments, the micelle has a diameter less than about 50 nm.

pH Responsive Compositions

In another aspect presented herein, are pH responsive compositions. The pH responsive compositions disclosed herein, comprise one or more pH-responsive micelles and/or nanoparticles that comprise block copolymers and a therapeutic agent. Each block copolymer comprises a hydrophilic polymer segment and a hydrophobic polymer segment wherein the hydrophobic polymer segment comprises an ionizable amine group to render pH sensitivity. This pH sensitivity is exploited to provide compositions suitable as drug-conjugate therapeutics.

The micelles may have different pH transition values within physiological range, in order to target specific cells or microenvironments. In some embodiments, the micelle has a pH transition value of about 5 to about 8, or any value therein. In some embodiments, the micelle has a pH transition value of about 5 to about 6. In some embodiments, the micelle has a pH transition value of about 6 to about 7. In some embodiments, the micelle has a pH transition value of about 7 to about 8. In some embodiments, the micelle has a pH transition value of about 6.3 to about 6.9. In some embodiments, the micelle has a pH transition value of about 5.0 to about 6.2. In some embodiments, the micelle has a pH transition value of about 5.9 to about 6.2. In some embodiments, the micelle has a pH transition value of about 5.0 to about 5.5. In some embodiments, the pH transition point is at 4.8, 4.9, 5.0, 5.1, 5.2, 5.3, 5.4, or 5.5. In some embodiments, the pH transition point is at about 4.8. In some embodiments, the pH transition point is at about 4.9. In some embodiments, the pH transition point is at about 5.0. In some embodiments, the pH transition point is at about 5.1. In some embodiments, the pH transition point is at about 5.2. In some embodiments, the pH transition point is at about 5.3. In some embodiments, the pH transition point is at about 5.4. In some embodiments, the pH transition point is at about 5.5.

The pH-sensitive micelle compositions of the present disclosure may advantageously have a narrow pH transition range, in contrast to other pH sensitive compositions in which the pH response is very broad (i.e. 2 pH units). In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the micelles have a pH transition range of less than about 0.25 pH unit. The narrow pH transition range advantageously provides a sharper pH response that can result in complete turn-on of the fluorophores with subtle changes of pH.

In some embodiments, the pH responsive compositions have an emission spectrum. In some embodiments, the emission spectrum is from 600-800 nm. In some embodiments, the emission spectrum is from 700-800 nm.

II. Methods of Use

Aerobic glycolysis, known as the Warburg effect, in which cancer cells preferentially uptake glucose and convert it into lactic acid or other acids, occurs in all solid cancers. Lactic acid or other acids preferentially accumulates in the extracellular space due to monocarboxylate transporters or other transporters. The resulting acidification of the extracellular space promotes remodeling of the extracellular matrix for further tumor invasion and metastasis.

Some embodiments provided herein describe compounds that form micelles at physiologic pH (7.35-7.45). In some embodiments, the compounds described herein are covantly or non-covalently conjugated to a therapeutic agent. In some embodiments, the micelle has a molecular weight of greater than $2\times10^7$ Daltons. In some embodiments, the micelle has a molecular weight of ~$2.7\times10^7$ Daltons. In some embodiments, the therapeutic agents are sequestered within the micelle core at physiologic pH (7.35-7.45) (e.g., during blood circulation). In some embodiments, when the micelle encounters an acidic environment (e.g., tumor tissues), the micelles dissociate into individual compounds with an average molecular weight of about $3.7\times10^4$ Daltons, allowing the release of the therapeutic agent. In some embodiments, the micelle dissociates at a pH below the pH transition point (e.g. the acidic state of tumor microenvironment).

In some embodiments, the therapeutic agent may be incorporated into the interior of the micelles. Specific pH conditions (e.g. acidic pH present in tumors and endocytic compartments) may lead to rapid protonation and dissociation of micelles into unimers, thereby releasing the therapeutic agent (e.g. a drug). In some embodiments, the micelle provides stable drug encapsulation at physiological pH (pH 7.4), but can quickly release the drug in acidic environments.

In some instances, the pH-sensitive micelle compositions described herein have a narrow pH transition range. In some embodiments, the micelles described herein have a pH transition range ($\Delta pH_{10-90\%}$) of less than 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the pH transition range is less than 0.25 pH units. In some embodiments, the pH transition range is less than 0.15 pH units. This sharp transition point allows the micelles to dissociate with the acid pH of the tumor microenvironment.

These micelles may be used as drug-delivery agents. Micelles comprising a drug may be used to treat e.g. cancers, or other diseases wherein the drug may be delivered to the appropriate location due to localized pH differences (e.g. a pH different from physiological pH (7.4)). In some embodiments, the disorder treated is a cancer. In some embodiments, the cancer comprises a solid tumor. In some embodiments, the tumor is a secondary tumor from metastasis of a primary tumor(s). In some embodiments, the drug-delivery may be to a lymph node or to a peritoneal or pleural surface.

In some embodiments is a method of treating a cancer in a subject in need thereof, comprising administering to the subject a therapeutically effective amount of any of the block copolymer, micelles or compositions disclosed herein.

In some embodiments, the cancer is a carcinoma, sarcoma, lymphoma, leukemia, melanoma, mesothelioma, multiple myeloma, or seminoma.

In some embodiments, the tumor is from a cancer. In some embodiments, the cancer is breast cancer, head and neck squamous cell carcinoma (NHSCC), lung cancer, ovarian cancer, prostate cancer, bladder cancer, kidney cancer, urethral cancer, esophageal cancer, colorectal cancer, peritoneal metastasis, or brain, skin (including melanoma and sarcoma). In some embodiments, the cancer is breast cancer, head and neck squamous cell carcinoma (NHSCC), esophageal cancer, renal cancer or colorectal cancer. In some embodiments, the cancer is breast cancer. In some embodiments, the cancer is head and neck squamous cell carcinoma (NHSCC). In some embodiments, the cancer is esophageal cancer. In some embodiments, the cancer is colorectal cancer.

In some embodiments, the cancer is a solid tumor.

In some embodiments, the tumor is reduced by about 5%, about 10%, about 15%, about 25%, about 30%, about 40%, about 50%, about 60%, about 70%, about 80%, or about 90%. In some embodiments, the tumor is reduced by about 50%. In some embodiments, the tumor is reduced by about 60%. In some embodiments, the tumor is reduced by about 70%. In some embodiments, the tumor is reduced by about 75%. In some embodiments, the tumor is reduced by about 80%. In some embodiments, the tumor is reduced by about 85%. In some embodiments, the tumor is reduced by about 90%. In some embodiments, the tumor is reduced by about 95%. In some embodiments, the tumor is reduced by about 99%.

In some embodiments, the cancer is not a solid tumor.

Methods of Dosing and Treatment Regimens

The pharmaceutical compositions of the present disclosure can be formulated to be compatible with the intended method or route of administration; exemplary routes of administration are set forth herein. In some embodiments, the pharmaceutical composition disclosed herein is in a form for dosing or administration by oral, intravenous (IV), intramuscular, subcutaneous, intratumoral, or intradermal injection. In some embodiments, the pharmaceutical composition is formulated for oral, intramuscular, subcutaneous, or intravenous administration. In some embodiments, the pharmaceutical composition in formulated for intravenous administration. In some embodiments, the pharmaceutical composition in formulated as an aqueous solution or suspension for intravenous (IV) administration. In some embodiments, the pharmaceutical composition is formulated to administer as a single dose. In some embodiments, the pharmaceutical compositions disclosed herein are formulated to administer as a bolus by IV. In some embodiments, the pharmaceutical compositions disclosed herein are formulated to administer by injection into the tumor.

In some embodiments, the compositions containing the compound disclosed herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

Typical dosages range from about 0.001 to about 100 mg/kg per dose. In some embodiments, the dose range is from about 0.01 to about 50 mg/kg. In some embodiments, further ranges of the dose are from about 0.05 to about 10 mg/kg per dose. In some embodiments, the dose is about 50 mg/kg. In some embodiments, the dose is about 100 mg/kg.

The exact dosage will depend upon the frequency and mode of administration, the gender, age, weight and general health of the subject treated, the nature and severity of the condition treated and any concomitant diseases to be treated and other factors evident to those skilled in the art.

In certain embodiments, the dose of composition being administered may be temporarily reduced or temporarily suspended for a certain length of time (i.e., a "drug holiday").

In some embodiments, the method comprises administering the composition once. In some embodiments, the method comprises administering the composition two or more times. In some embodiments, the composition is administered once per day.

In some embodiments, the subject is a mammal. In some embodiments, the subject is a human.

Combination Therapy

In another aspect, the compositions disclosed herein are administered with one or more additional therapies. In some embodiments, the method further comprises a second anti-cancer therapy. In some embodiments, the second anti-cancer therapy is surgery, chemotherapeutic, radiation therapy, gene therapy, or immunotherapy. In some embodiments, the second anti-cancer therapy is an immunotherapy. In some embodiments, the immunotherapy is a checkpoint therapy. In some embodiments, the second anti-cancer therapy is radiation therapy. In some embodiments, the second therapy is surgery.

III. Methods of Encapsulation

In another aspect described herein, is a method for increasing encapsulation of a therapeutic agent into a micelle, comprising conjugating the therapeutic agent with a fluorescent dye.

In some embodiments, the method further comprising contacting the conjugated therapeutic agent with a block copolymer to form the micelle.

In some embodiments, the therapeutic agent is a protein of about 5 to about 20 KDa.

In some embodiments, the protein is a cytokine or fragment thereof. In some embodiments, the cytokine is an IL-2, IL-1, IL-3, IL-4, IL-5, IL-6, IL-7, IL-8, IL-9, IL-10, IL-11, IL-12, IL-13, IL-15, IL-17, or IL-18 protein or a fragment thereof.

In some embodiments, the therapeutic agent is an antibody or a fragment thereof. In some embodiments, the antibody or fragment thereof is a bispecific antibody or a fragment thereof. In some embodiments, the bispecific antibody or fragment thereof is a fusion protein. In some embodiments, the fusion protein is a bi-specific T-cell engager (BiTE).

In some embodiments, the fluorescent dye has an excitation spectrum from about 400 nm to about 900 nm. In some embodiments, the fluorescent dye has an excitation spectrum about: 400, 450, 500, 550, 600, 650, 700, 750, 800, or 850 nm.

In some embodiments, the fluorescent dye is coumarin, rhodamine, cyanine, xanthene, fluorescein, or a sulfonated or negatively charged form thereof, or a compound from FIG. 22.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, butyl, s-butyl, n-pentyl, 1,1-dimethylethyl (t-butyl), 3-methylhexyl, 2-methylhexyl, 1-ethyl-propyl, and the like. In some embodiments, the alkyl is methyl, ethyl, s-butyl, or 1-ethyl-propyl. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a 0, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —$OCH_2OMe$, —$OCH_2CH_2OMe$, or —$OCH_2CH_2OCH_2CH_2NH_2$. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthalenyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —$CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

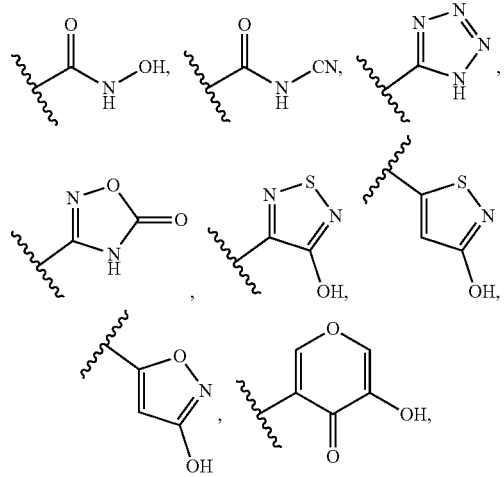

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. In some embodiments, a cycloalkyl is a $C_3$-$C_6$ cycloalkyl. In some embodiments, a cycloalkyl is a 3- to 6-membered cycloalkyl. Representative cycloalkyls include, but are not limited to, cycloakyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. In some embodiments, the heterocycloalkyl is a $C_2$-$C_7$ heterocycloalkyl. In some embodiments, the heterocycloalkyl is a $C_2$-$C_6$ heterocycloalkyl. In some embodiments, the heterocycloalkyl is a $C_2$-$C_5$ heterocycloalkyl. In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 3- to 5-membered heterocycloalkyl. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

Heteroaryl" refers to an aryl group that includes one or more ring heteroatoms selected from nitrogen, oxygen and sulfur. The heteroaryl is monocyclic or bicyclic. In some embodiments, the heteroaryl is a 5- or 6-membered heteroaryl. In some embodiments, the heteroaryl is a 5-membered heteroaryl. In some embodiments, the heteroaryl is a 6-membered heteroaryl. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —CO$_2$H, —CO$_2$alkyl, nitro, and amino, including mono- and di-substituted amino groups (e.g., —NH$_2$, —NHR, —N(R)$_2$), and the protected derivatives thereof. In some embodiments, optional substituents are independently selected from alkyl, alkoxy, haloalkyl, cycloalkyl, halogen, —CN, —NH$_2$, —NH(CH$_3$), —N(CH$_3$)$_2$, —OH, —CO$_2$H, and —CO$_2$alkyl. In some embodiments, optional substituents are independently selected from fluoro, chloro, bromo, iodo, —CH$_3$, —CH$_2$CH$_3$, —CF$_3$, —OCH$_3$, and —OCF$_3$. In some embodiments, optional substituents are independently selected from fluoro, chloro, —CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

"Pharmaceutically acceptable," as used herein, refers a material, such as a carrier or diluent, which does not abrogate the biological activity or properties of the block copolymer, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M.

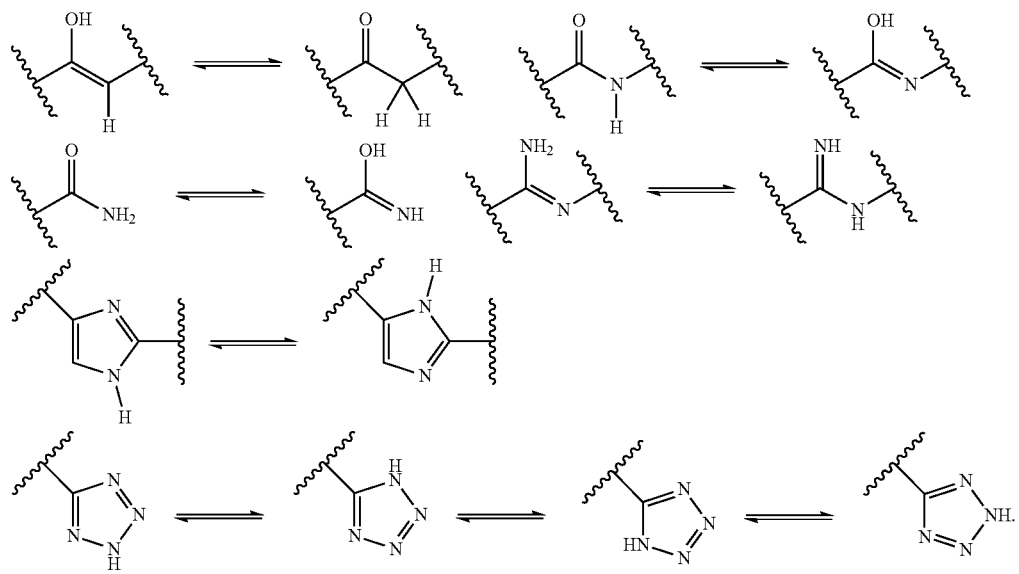

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a block copolymer with an acid. In some embodiments, the block copolymer disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a block copolymers disclosed herein are prepared as a chloride salt, sulfate salt, bromide salt, mesylate salt, maleate salt, citrate salt or phosphate salt.

In some embodiments, pharmaceutically acceptable salts are obtained by reacting a block copolymer disclosed herein with a base. In some embodiments, the block copolymer disclosed herein is acidic and is reacted with a base. In such situations, an acidic proton of the block copolymer disclosed herein is replaced by a metal ion, e.g., lithium, sodium, potassium, magnesium, calcium, or an aluminum ion. In some cases, block copolymers described herein coordinate with an organic base, such as, but not limited to, ethanolamine, diethanolamine, triethanolamine, tromethamine, meglumine, N-methylglucamine, dicyclohexylamine, tris (hydroxymethyl)methylamine. In other cases, block copolymers described herein form salts with amino acids such as, but not limited to, arginine, lysine, and the like. Acceptable inorganic bases used to form salts with block copolymers that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the block copolymers provided herein are prepared as a sodium salt, calcium salt, potassium salt, magnesium salt, melamine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of block copolymers described herein, as well as, active metabolites of these compounds having the same type of activity.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

As used herein, "pH responsive system," "pH responsive composition," "micelle," "pH-responsive micelle," "pH-sensitive micelle," "pH-activatable micelle" and "pH-activatable micellar (pHAM) nanoparticle" are used interchangeably herein to indicate a micelle comprising one or more compounds, which disassociates depending on the pH (e.g., above or below a certain pH). As a non-limiting example, at a certain pH, the block copolymers of Formula (III) is substantially in micellar form. As the pH changes (e.g., decreases), the micelles begin to disassociate, and as the pH further changes (e.g., further decreases), the block copolymers of Formula (III) is present substantially in disassociated (non-micellar) form.

As used herein, "pH transition range" indicates the pH range over which the micelles disassociate.

As used herein, "pH transition value" (pH) indicates the pH at which half of the micelles are disassociated.

A "nanoprobe" is used herein to indicate a pH-sensitive micelle which comprises an imaging labeling moiety. In some embodiments, the labeling moiety is a fluorescent dye. In some embodiments, the fluorescent dye is indocyanine green dye.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally. In some embodiments, the compositions described herein are administered intravenously.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the standard deviation of error for the device or method being employed to determine the value, for example ±10% of a referred value. Following longstanding patent law, the words "a" and "an," when used in conjunction with the word "comprising" in the claims or specification, denotes one or more, unless specifically noted.

EXAMPLES

Example 1. Synthesis of Block Copolymers

General Synthetic Methods

Block copolymers and micelles described herein are synthesized using standard synthetic techniques or using methods known in the art.

Unless otherwise indicated, conventional methods of mass spectroscopy, NMR, HPLC, protein chemistry, biochemistry, recombinant DNA techniques and pharmacology are employed. Block copolymers are prepared using standard organic chemistry techniques such as those described in, for example, March's Advanced Organic Chemistry, 6$^{th}$ Edition, John Wiley and Sons, Inc. Some abbreviations used herein are as follows:
  DCM: dichloromethane
  DMAP: 4-dimethylaminopyridine
  DMF: dimethyl formamide
  DMF-DMA: N,N-dimethylformamide dimethyl acetal
  EDCI: 1-ethyl-3-(3-dimethylaminopropyl) carbodiimide
  EtOAc: ethyl acetate
  EtOH: ethanol
  ICG-OSu: indocyanine green succinamide ester
  MeOH: methanol
  PMDETA: N,N,N',N'',N''-Pentamethyldiethylenetriamine
  CDI carbonyldiimidazole
  NHS-Carbonate N-hydroxysuccinimide carbonate
  SPDB N-succinimidyl-4-(2-pyridyldithio)butanoate
  TEA: triethyl amine
  Hr Hour(s)
  ISR Incurred sample reanalysis
  IV Intravenous
  kg Kilogram
  mg Milligram(s)
  mL Milliliters(s)
  μg Microgram(s)
  NC Not calculated
  NR Not reported Suitable PEG polymers may be purchased (for example, from Sigma Aldrich) or may be synthesized according to methods known in the art. In some embodiments, the hydrophilic polymer can be used as an initiator for polymerization of the hydrophobic monomers to form a block copolymer. For example, MPC polymers (e.g. narrowly distributed MPC polymers) can be prepared by atom transfer radical polymerization (ATRP) with commercially available small molecule initiators such as ethyl 2-bromo-2-methylpropanoate (Sigma Aldrich). These resulting MPC polymers can be used as macromolecular ATRP initiators to further copolymerize with other monomers to form block polymers can be synthesized using atom transfer radical polymerization (ATRP) or reversible addition-fragmentation chain transfer (RAFT) methods.

In some embodiments, suitable block copolymers and micelles may be synthesized using standard synthetic techniques or using methods known in the art in combination with methods described in patent publications numbers WO 2012039741 and WO 2015188157, which are herein incorporated by reference in their entirety.

Example 2. Micelle Formation

General Methods

Methanol is added to the block copolymer in a glass round bottom flask and dissolved with the aid of a sonication bath. After dissolution, the resulting solution is quantitatively transferred to a HDPE bottle containing a stir bar and cooled to 0° C. with an ice-bath. Water is added dropwise while stirring, to the methanolic polymer solution in the HDPE bottle using a peristaltic pump. The HDPE bottle containing the polymer solution is maintained in the ice bath, resulting in the formation of micelles. Methanol is removed from the micelle solution using 5 cycles of tangential flow filtration (TFF) through a 100k Pellicon® 2 Mini Ultrafiltration Module.

PEG-PDBA-IL-2 Formulations Prepared by Simple Mixing

Polymer micelle solution in water was diluted with injectable water (WFI). 10% (w/w) of IL-2 (% of polymer) in phosphate buffer was added to make a solution of 1 mg/mL micelle and 0.1 mg/mL IL-2 by pipette mixing. The solution was incubated at room temperature for 10 minutes. Then the sample was centrifuged at high-speed in a microcentrifuge at ambient temperature (Eppendorf, 21,130×g, 10 mins.). The solution was purified by membrane ultrafiltration (Amicon, 0.5 mL, MWCO 100 kDa) to remove any unencapsulated IL-2. Then 0.5 mL of the formulation was added to an Amicon ultracentrifugation device and centrifuged at 5,000 rcf for 2-3 minutes. The permeate was discarded and the retentate which contained the micelle-IL-2 formulation was diluted to 0.5 mL in water for injection. This process was repeated 10 times. The IL-2 concentration in the formulation was determined by western blot or dot blot against a standard curve.

Purification of PDBA-IL-2 Formulations by FPLC

PEG-PDBA-IL-2 non-covalent formulations or conjugates by one of the methods (e.g. simple mixing, acid-base titration, etc.). Crude PDBA-IL-2 formulations were purified by FPLC using an Akta Pure 25M (GE) system equipped with a Superdex 200 Increase 10/300 GL column (GE). Equilibration was performed at 0.75 mL/minute in 1×PBS. Sample injection was performed using an appropriated sized sample loop or super loop. Isocratic elution was performed in 1×PBS at 0.5 mL/minute flow rate while monitoring absorbance at multiple wavelengths (e.g. 214 nm, 280 nm, 700 nm). Fractions (0.5 mL) were collected in 1.5 mL tubes. Fractions containing formulation and free protein as indicated by the chromatogram were analyzed by SDS-PAGE, western blot or dot blot. Fractions containing IL-2 in formulations were pooled.

PEG-PDBA-IL-2 Formulations Double Emulsion Solvent Evaporation (DESE)

A 1.0 mg/mL of polymer solution in dichloromethane (DCM) and 1.0 mg/mL of IL-2 in phosphate buffer was chilled in an ice-water bath for 5 min. IL-2 solution was added to the polymer solution dropwise with 10% (w/w, IL-2/polymer) total amount under sonication condition in ice-water bath to form the first emulsion solution. The first emulsion was added dropwise to a chilled PVA/THL solution under sonication condition in ice-water to form the second emulsion solution. The second emulsion solution was stirred overnight at room temperature. The solution was purified by membrane ultrafiltration (Amicon, 0.5 mL, MWCO 100 kDa) to remove unencapsulated IL-2. Then 0.5 mL of formulation was added to an Amicon ultracentrifugation device and centrifuged at 5,000 rcf for 2-3 minutes. The permeate was discarded and the retentate which contained the micelle-IL-2 formulation was diluted to 0.5 mL in water for injection. This process was repeated 10 times. IL-2 concentration in the formulation was determined by western blot or dot blot against a standard curve.

PEG-PDBA-IL-2 Formulations by Acid-Base Titration

To a polymer solution in pH 4.47 phosphate buffer, 10% (w/w) IL-2 in phosphate buffer was added and vortexed at room temperature. 1M NaOH solution was added to the solution under sonication condition. The solution was diluted with the final concentration of 1.0 mg/mL polymer and 0.1 mg/mL IL-2 by WFI. The solution was purified by membrane ultrafiltration (Amicon, 0.5 mL, MWCO 100 kDa) to remove unencapsulated IL-2. Next 0.5 mL of the formulation was added to an Amicon ultracentrifugation device and centrifuged at 5,000 rcf for 2-3 minutes. The permeate was discarded and the retentate which contained the micelle-IL-2 formulation was diluted to 0.5 mL in water for injection. This process was repeated 10 times. IL-2 concentration in the formulation was determined by western blot or dot blot against a standard curve.

Quantitation of IL-2 and Micelle in Formulations by Dot Blot

The IL-2 content and micelle content of formulations was determined by dot blot. The Dot-Blot apparatus was assembled with a 0.2 μm nitrocellulose membrane. Each well was washed with 200 μL 1× PBS under vacuum followed by rehydration with 100 μL PBS. Samples and standards (10-100 μL) were added and a vacuum was applied to the membrane. The membrane was washed 2× with PBS.

IL-2 immunoblotting was performed by probing and by blocking with PBS-T (PBS with 0.05% Tween-20) supplemented with 2% BSA, probing with anti-IL-2 rabbit monoclonal antibody (Invitrogen, 2H20L7, 1:1000 dilution in PBS-T, 1 hour), washing 4 times with PBS-T, followed by probing with Donkey-anti-Rabbit IgG labelled with IRDye® 680RD (LI-COR, 1:5000 dilution in PBS-T). Detection was performed by using a ChemiDoc MP (Bio-Rad) and images were quantitated by densitometry analysis using ImageLab (Bio-Rad). IL-2 content was determined by fitting to a standard curve.

Polymer content was determined by immunoblotting for poly-ethylene glycol against a polymer standard curve. Immunoblotting was performed by blocking the membrane with PBS supplemented with 2% BSA, probing with THE™ anti-PEG IGM mAb (Genscript, 1:1000 dilution in PBS), washing 4 time with PBS, probing with goat anti-mouse IgM (μ chain specific) labelled with IRDye® 680RD (LI-COR, 1:5000 dilution in PBS). Detection was performed by using a ChemiDoc MP (Bio-Rad) and images were quantitated by densitometry analysis using ImageLab (Bio-Rad). Polymer content was determined by fitting to a PEG-PDBA standard curve.

Example 3. General Procedure for In Vivo Tumor Mouse Models

Female NOD scid mice (Strain NOD.CB17-Prkdc$^{scid/J}$) aged approximately 6-8 weeks were inoculated in the submandibular triangle with $1.5 \times 10^6$ HN5 tumor cells in 50 μL 1× PBS and tumors were allowed to grow for ~1 week. PEG-PDBA-IL-2 or PEG-PDBA-Fab formulations were prepared with rhIL-2 that was fluorescently labeled with IRDye® 800CW (LiCOR) and dosing was normalized by 800CW fluorescence ($\lambda_{Ex}$ 760 nm, $\lambda_{Em}$ 780 nm) using a plate reader. Unencapsulated fluorescently labeled protein was used as a control. Micelle-IL-2 formulations or proteins were administered via tail vein injection. Animals were anesthetized using isoflurane and in vivo small animal imaging was performed using a Pearl Trilogy (LI-COR) in the white light and 800 nm channels at 1 hour, 3 hours, and 24 hours after test article administration. After the final in vivo imaging time point, animals were sacrifice by $CO_2$ asphyxiation and cervical dislocation, and ex vivo imaging of major organs was performed. Fluorescence was quantitated by ROI analysis using ImageStudio software (LI-COR).

Example 4. General Procedures for In Vitro IL-2 Bioactivity Assay

IL-2 bioactivity in formulations was measured using the thaw-and-use IL-2 Bioassay (Promega) according to the manual. Micelles encapsulating IL-2 or conjugated to IL-2 were evaluated in dose-response assays in either acid-released or encapsulated states. Acid release was performed by mixing 20 μL of formulation with 20 μL of pooled human serum, followed by 40 μL acidic sodium acetate buffer (0.1 M sodium acetate, 0.9% saline, pH ~4.5) incubating for 15 minutes at RT, and subsequently 40 μL 20× PBS was added. For encapsulated samples, acidic acetate buffer was substituted with neutral acetate buffer (0.1M sodium acetate, 0.9% saline, pH 7-7.6) and mixed using a similar process. Three-fold serial dilutions of released or encapsulated formulations were prepared in assay buffer (90% RPMI 1640/10% Fetal Bovine Serum). Formulation dilutions (25 μL) were added to wells containing IL-2 bioassay cells pre-seeded in in white opaque 96-well microplates or half-well microplates (Corning) according to the manufacturer recommendations. Assay buffer alone and cells without treatment were used as negative controls, while IL-2 alone was used as a positive control. The plates were covered and incubated for 6 hours in a humidified incubator (37° C., 5% $CO_2$). After incubation, 75 μL Bio-Glo reagent (Promega) was added, incubated for 10 minutes and the bioluminescence was read using a plate reader (Tecan M200 Pro). Data was plotted in Prism (GraphPad) and ED50 was calculated by non-linear fit.

Example 5. General Procedure for SDS-PAGE Analysis of Formulation

Micelle-IL-2 formulations were evaluated by SDS-PAGE to confirm IL-2 loading into micelles and IL-2 integrity. Samples were prepared to target 100-200 ng protein loaded per lane. For characterization of IL-2 loaded formulation purification by FPLC, the load sample constitutes the crude formulation without any purification, the spun load samples constitutes the formulation after purification by high-speed centrifugation to clear aggregates and large particles, the micelle pool is prepared by combining fractions containing micelles and the free IL-2 sample contains fractions containing unencapsulated protein. Formulation samples were diluted in 4× Laemmli buffer (Bio-Rad) with or without β-mercaptoethanol depending on the reducing requirements and denatured at 65° C. for 5 minutes. Samples were loaded in Any kD™ or 4-20% SDS-PAGE gradient Mini-Protean gels (Bio-Rad) by stacking at 50V for 30 minutes followed by separating at 100V for 90 minutes. Detection of IL-2 was performed by Simply Blue Stain (Invitrogen). IL-2 was also determined by western blot after transfer to 0.2 μm nitrocellulose membrane by probing with anti IL-2 Ab clone (Cell Signaling Technology, Clone D7A5, 1:4000 dilution) followed by HRP-conjugated anti-rabbit secondary (LI-COR, 1:2000 dilution) and detected by ECL reagent (Pierce) and chemiluminescence was captured with ChemiDoc MP imager (Bio-Rad). Image processing and densitometry analysis was performed using ImageLab (Bio-Rad). If required, quantitation of IL-2 was performed by fitting to an IL-2 standard curve.

Example 6. Methods of Treatment

Human subjects suffering cancer (e.g., solid tumor cancer) are administered with a therapeutically effective amount of a therapeutic agent encapsulated by the block copolymer as disclosed herein (e.g., in a form of micelle) by injection, for example by intravenous injection or in a range of 1 mg/kg to 100 mg/kg for example 50 mg/kg to 100 mg/kg.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A micelle comprising:
   (i) a block copolymer of Formula (III), or a pharmaceutically acceptable salt, solvate, or hydrate thereof:

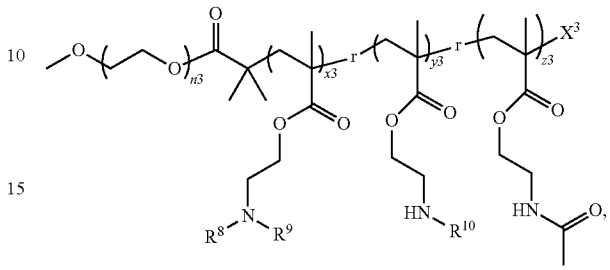

Formula (III)

wherein:
   $n_3$ is an integer from 10-200;
   $x_3$ is an integer from 40-300;
   $y_3$ is an integer from 1-6;
   $z_3$ is an integer from 1-10;
   $X^3$ is a halogen, —OH, or —C(O)OH;
   $R^8$ and $R^9$ are each independently an optionally substituted $C_1$-$C_6$ alkyl, $C_3$-$C_{10}$ cycloalkyl or aryl;
   or $R^8$ and $R^9$ are taken together with the corresponding nitrogen to which they are attached to form an optionally substituted 5 to 7-membered ring; and
   $R^{10}$ is indocyanine green; and
(ii) a therapeutic agent encapsulated by the block copolymer, wherein the therapeutic agent is a protein conjugated to the indocyanine green.

2. The micelle of claim 1, wherein $R^8$ and $R^9$ are each independently an optionally substituted $C_1$-$C_6$ alkyl.

3. The micelle of claim 1, wherein $R^8$ and $R^9$ are each independently —$CH_2CH_3$, —$CH_2CH_2CH_3$, or —$CH_2CH_2CH_2CH_3$.

4. The micelle of claim 1, wherein $R^8$ and $R^9$ are each —$CH_2CH_2CH_2CH_3$.

5. The micelle of claim 1, wherein $R^8$ and $R^9$ taken together are —$CH_2(CH_2)_2CH_2$—, —$CH_2(CH_2)_3CH_2$—, or —$CH_2(CH_2)_4CH_2$—.

6. The micelle of claim 1, wherein $x_3$ is an integer from 50-200, 60-160, or 90-140.

7. The micelle of claim 6, wherein $x_3$ is 90-140.

8. The micelle of claim 1, wherein $y_3$ is an integer from 1-6, 1-5, 1-4, or 1-3.

9. The micelle of claim 1, wherein $z_3$ is an integer from 1-9, 1-8, 1-7, 1-6, 1-5, 1-4, or 1-3.

10. The micelle of claim 1, wherein $n_3$ is an integer from 60-150 or 100-140.

11. The micelle of claim 10, wherein $n_3$ is 100-140.

12. The micelle of claim 1, wherein $X^3$ is a halogen.

13. The micelle of claim 12, wherein $X^3$ is —Br.

14. The micelle of claim 1, wherein the protein is a protein of about 5 to about 20 KDa optionally a cytokine or fragment thereof, or is an antibody optionally an engineered antibody, or a fragment thereof.

15. The micelle of claim 14, wherein the cytokine is an interleukin (IL), chemokine, interferon, lymphokine, monokine, colony stimulating factor, or tumor necrosis factor, optionally an IL-2, IL-1, IL-3, IL-4, IL-5, IL-6, IL-7, IL-8, IL-9, IL-10, IL-11, IL-12, IL-13, IL-15, IL-17, or IL-18 protein, or a fragment thereof.

16. A micelle comprising:
(i) a block copolymer of Formula (IV), or a pharmaceutically acceptable salt, solvate, or hydrate thereof:

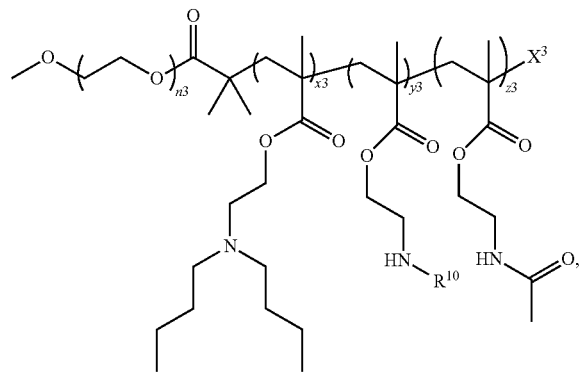

Formula (IV)

wherein:
- $n_3$ is an integer from 10-200;
- $x_3$ is an integer from 40-300;
- $y_3$ is an integer from 1-6;
- $z_3$ is an integer from 1-10;
- $R^{10}$ is indocyanine green; and
- $X^3$ is a halogen, —OH, or —C(O)OH; and (ii) a therapeutic agent encapsulated by the block copolymer, wherein the therapeutic agent is a protein conjugated to the indocyanine green.

17. A method for increasing encapsulation of a therapeutic agent into a micelle, the micelle comprising a block copolymer of Formula (III), or a pharmaceutically acceptable salt, solvate, or hydrate thereof:

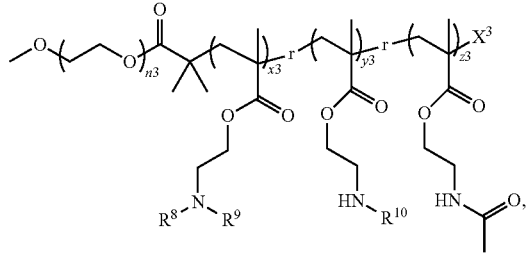

Formula (III)

wherein:
- $n_3$ is an integer from 10-200;
- $x_3$ is an integer from 40-300;
- $y_3$ is an integer from 1-6;
- $z_3$ is an integer from 1-10;
- $X^3$ is a halogen, —OH, or —C(O)OH;
- $R^8$ and $R^9$ are each independently an optionally substituted $C_1$-$C_6$ alkyl, $C_3$-$C_{10}$ cycloalkyl or aryl;
- or $R^8$ and $R^9$ are taken together with the corresponding nitrogen to which they are attached to form an optionally substituted 5 to 7-membered ring; and
- $R^{10}$ is indocyanine green;

the method comprising conjugating the therapeutic agent with the indocyanine green.

18. The micelle of claim 1, wherein $R^8$ and $R^9$ are taken together with the corresponding nitrogen to which they are attached to form an optionally substituted 5 to 7-membered ring.

* * * * *